US006586438B2

(12) United States Patent
Piper

(10) Patent No.: US 6,586,438 B2
(45) Date of Patent: *Jul. 1, 2003

(54) ANTIDIABETIC FORMULATION AND METHOD

(75) Inventor: Beth Anne Piper, Hopewell, NJ (US)

(73) Assignee: Bristol-Myers Squibb Co., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/432,465

(22) Filed: Nov. 3, 1999

(65) Prior Publication Data

US 2002/0177602 A1 Nov. 28, 2002

(51) Int. Cl.$^7$ .................. A61K 31/495; A61K 31/445; A61K 31/175; A61K 31/155

(52) U.S. Cl. ...................... 514/255; 514/315; 514/326; 514/412; 514/423; 514/439; 514/58; 514/635; 514/866

(58) Field of Search ................... 514/635, 593, 514/255, 315, 326, 412, 423, 439, 866

(56) References Cited

U.S. PATENT DOCUMENTS

| | | |
|---|---|---|
| 3,174,901 A | 3/1965 | Sterne |
| 3,979,520 A | 9/1976 | Rothe et al. |
| 4,060,634 A | 11/1977 | Rothe et al. |
| 4,916,163 A | 4/1990 | Ni |
| 5,631,224 A | 5/1997 | Efendic et al. |
| 5,663,198 A | 9/1997 | Reul et al. |
| 5,922,769 A | 7/1999 | Barelli et al. |
| 5,965,584 A | 10/1999 | Ikeda et al. |
| 6,153,632 A | 11/2000 | Rieveley |
| 6,303,146 B1 | 10/2001 | Bonhomme et al. |

FOREIGN PATENT DOCUMENTS

| | | |
|---|---|---|
| EP | 0362704 B2 | 8/1996 |
| EP | 0749751 | 12/1996 |
| WO | 97/17975 | 5/1997 |
| WO | 98/56378 | 12/1998 |
| WO | 98/57634 | 12/1998 |
| WO | 99/03476 | 1/1999 |
| WO | 99/20275 | 4/1999 |
| WO | 99 29314 A | 6/1999 |
| WO | 99/43705 | 9/1999 |

OTHER PUBLICATIONS

Earle et al. Acta Diabetol, 36: 61–65, 1999.*
Hermann, L.S. et al, Diabetic Medicine, 11/10 pp. 953–960, 1994.
D'Argenzio, R. et al, Minerva Endocrinologia, vol. 21, No. 3, Sep. 1996.
Hermann et al, Therapeutic comparison of metformin and sulfonylurea, alone and in various combinations. A double–blind controlled study. Diabetes Care, 17:1100–1109 (1994).
Aviles–Santa et al, Ann. Intern. Med., 131(3):182–188 (1999).
Daniel et al, Ann. Pharmacother., 31(4):474–480 (1997).
Scheen, Diabetes and Metabolism, 24(4):311–321 (1998).
Ratner, Today's Therapeutic Trends, 17/1:57–66, (1999).
Maislos et al, Diabetologia, 42, suppl. 1: A223, (1999).
Wolffenbuttel, Neth. J. Med., 55(5): 229–234, (1999).
Paul, Arzneim.–Forsch., 49(10):835–842, (1999).
Scheen et al, Diabetes Care, 22(9):1568–1577, (1999).
Greene, Expert Opin. Invest. Drugs, 8(10):1709–1719, (1999).
Karara et al, Pharmaceutical Research, vol. 14, No. 11, Suppl: S557, (1997).
Fonseca et al, Diabetes, 48, Suppl.1: A100, (1999).
Suzuki et al, Diabetes, 48, Suppl.1: A454, (1999).
Vigneri et al, "Treatment of NIDDM Patients with Secondary Failure to Glyburide: Comparison of the Addition of Either Metformin or Bed–Time NPH Insulin to Glyburide", Diabete & Metabolisme, 1991, 17, 232–234.
Higginbotham et al, "Double–Blind Trial of Metformin in the Therapy of Non–Ketotic Diabetes", The Med. Journal of Australia, Aug. 11, 1979, 154–156.
Edwards et al, Combination Glipizide/Metformin Treatment Reduces Low Density Lipoprotein Binding to Arterial Proteglycane in NIDDM, Diabetes, (46, Suppl. 1, 45A, 1997).
Cefalu et al, "Combination of glipizide/Metformin Normalizes Glucose and Improves Insulin Sensitivity in Hyperinsulinemia Moderately Well Controlled", Diabetes (45, Suppl. 2, 201A, 1996).
Crouse et al, "Effects of Combination of Glipizide/Metformin Treatment on Oxidizability of LDL in NIDDM", Circulation (94, No. 8, Suppl., 1508, 1996).

(List continued on next page.)

Primary Examiner—Rebecca Cook
(74) Attorney, Agent, or Firm—Burton Rodney; Maureen P. O'Brien

(57) ABSTRACT

A low dose antidiabetic pharmaceutical formulation is provided, especially adapted for treating Type II diabetes in drug naive patients, which includes a combination of metformin (employed in a reduced amount (less than 800 mg metformin per day) compared to that employed in generally accepted medical practice) and at least one other antidiabetic agent such as a sulfonyl urea, for example, glyburide, which combination provides at least about substantially equivalent efficacy in treating diabetes in drug naive patients, as do antidiabetic formulations containing metformin employed in dosages prescribed in generally accepted medical practice for first line therapy in treating diabetes, but with substantially reduced side effects, such as hypoglycemia and/or gastrointestinal distress. A method for treating diabetes in drug naive human patients is also provided employing the above formulation to reduce insulin resistance and/or postprandial glucose excursion and/or hemoglobin 1Ac, and/or increase post-prandial insulin, thereby treating the diabetes.

7 Claims, 10 Drawing Sheets-

OTHER PUBLICATIONS

Cefalu et al, "Insulin Sensitivity is Improved After Glipizide Monotherapy and Combination with Metformin", Diabetologia (39, Suppl. 1, A231, 1996).

Reaven et al, "Combined Metformin–Sulfonylurea Treatment of Patients with Noninsulin–Deendent Diabetes in Fair to Poor Glycemic Control", J. Clin. Endocrinol. Metab. (74, No. 5, 1020–26, 1992).

Hollenbeck et al, "Combination Glipizide/Metformin Treatment in Non–Insulin Dependent Daibetes (NIDDM)", Diabetes (39, Suppl. 1, 108A, 1990).

Press Release Sep. 30, 1999: Bristol–Myers Squibb Files New Drug Application for Novel Oral Antidiabetic Drug.

GLUCOMIDE—Italian Package Insert, Repertorio Farmaceutico Italiano, 1999—with English translation.

GLIBOMET—Italian Package Insert, Repertorio Farmaceutico Italiano, 1999—with English translation.

SUGUAN M—Italian Package Insert, Repertorio Farmaceutico Italiano, 1999—with English translation.

BI–EUGLUCON M—Italian Package Insert, Repertorio Farmaceutico Italiano, 1999—with English translation.

Abstract AU 42302/89 Sep. 28, 1989.

Haupt et al, "Oral Antidiabetic Combination Therapy with Sulfonyl Ureas and Metformin", Med. Welt. (40, No. 5, 118–23, 1989).

Parodi et al, "Results with a Combination of Glipizide and Diemethylbiguanide in 40 Cases of Diabetes", Gass. Med. Ital., 132/5 (226–235) 1973.

* cited by examiner

ANTIDIABETIC FORMULATION AND METHOD

FIELD OF THE INVENTION

The present invention relates to a low dose pharmaceutical formulation for treating type 2 diabetes in drug naive patients, which includes metformin (preferably employed in reduced amounts compared to that employed in generally accepted medical practice) and another antidiabetic agent such as a sulfonyl urea, for example, glyburide, which formulation has at least substantially equivalent efficacy in treating type 2 diabetes as compared to prior art antidiabetic formulations containing metformin, but with substantially reduced side effects, and to a method for treating diabetes employing such formulations.

BACKGROUND OF THE INVENTION

The biguanide antihyperglycemic agent metformin disclosed in U.S. Pat. No. 3,174,901 is currently marketed in the U.S. in the form of its hydrochloride salt (Glucophage®), Bristol-Myers Squibb Company).

The diagnosis and management of type 2 diabetes mellitus is rapidly undergoing progressive changes. It is now widely accepted that glycemic control makes a difference. The goal of diabetes therapy today is to achieve and maintain as near normal glycemia as possible to prevent the long-term microvascular and macrovascular complications of an elevated blood glucose. The diagnosis of diabetes has undergone significant changes as evidenced by the new ADA diagnostic and classification guidelines. Oral therapeutic options for the treatment of type 2 diabetes mellitus, until recently, have been severely limited. Prior to 1995, sulfonyl ureas had been the mainstay of oral diabetes agents in the United States. Sulfonyl ureas target one mechanism of hyperglycemia by augmenting insulin secretion from the beta cell. Since 1995, three new classes of agents have been added to the anti-diabetes armamentarium for the management of hyperglycemia. Metformin, a biguanide, targets additional mechanisms of hyperglycemia by inhibiting hepatic glucose production and enhancing peripheral glucose uptake and thereby reduce insulin resistance; thiazolidinediones such as troglitazone, rosiglitazone and pioglitazone decrease peripheral insulin resistance; and alpha-glucosidase inhibitors such as acarbose and miglitol help control postprandial glucose excursion by delaying absorption of dietary carbohydrate. These agents are all indicated as monotherapy and some are indicated for use in combination therapy, generally, after monotherapy has been found to be inadequate.

In 1995, metformin was added to sulfonyl urea therapy n patients who had not achieved glycemic control with sulfonyl urea monotherapy and the two agents were found to have a remarkable effect on glycemic control or lowering of hemoglobin-A1c. The different mechanisms of action in targeting hyperglycemia are complimentary and make combination use attractive and a rational course of action. Prescription data reveals approximately 60% of metformin use is in combination with a sulfonyl urea.

Examples of combinations of metformin and the sulfonyl urea glyburide (also referred to as glibenclamide) are disclosed in the following references.

(1) WO 97/17975 published May 22, 1997, (Barelli et al, Istituto Gentili S.P.A.) (hereinafter Barelli et al) discloses a combination of glibenclamide and metformin in a 1:100 weight ratio, so as to allow a daily dosage of 15 mg glibenclamide and 1500 mg metformin, used for the onset of diabetes to the most severe cases, particular in cases of secondary failure to a combination of glibenclamide-metformin HCl in a weight ratio higher than 1:100.

(2) Vigneri et al, Treatment of NIDDM Patients with Secondary Failure to Glyburide: Comparison of the Addition of Either Metformin or Bed-Time NPH Insulin to Glyburide, Diabete & Metabolisme, 1991, 17, 232–234, disclose use of a combination of 1.5 g/day metformin and 15 mg/day glyburide to treat NIDDM patients with secondary failure to 15 mg/day glyburide.

(3) Higginbotham et al, Double-Blind Trial of Metformin in the Therapy of Non-Ketotic Diabetes, The Medical Journal of Australia, Aug. 11, 1979, 154–156, discloses treatment of diabetic patients, who were already receiving from 10 mg to 20 mg per day of glibenclamide, with 500 mg metformin twice a day. Higginbotham et al conclude "that in selected diabetics whose condition is inadequately controlled with sulphonylurea therapy, significant improvement in diabetic control can be obtained by the addition of metformin in a low dose of 500 mg twice a day."

(4) U.S. application Ser. No. 09/353,141, filed Jul. 14, 1999 (based on European application No. 98401781.4, filed Jul. 15, 1998) discloses formulations containing metformin and glyburide where the glyburide is of a particular particle size as described hereinafter.

References which disclose combinations of metformin and glipizide include the following:

(1) Combination of glipizide/metformin treatment reduces low density lipoprotein binding to arterial proteglycans in DIDDM, Edwards et al, Diabetes, (46, Suppl. 1, 45A, 1997).

(2) Combination of glipizide/metformin normalizes glucose and improves insulin sensitivity in hyperinsulinemia moderately well controlled. Cefalu et al, Diabetes, (45, Suppl. 2, 201A, 1996).

(3) Effects of combination of glipizide/metformin treatment on oxidizability of LDL in NIDDM, Crouse et al, Circulation, (94, No. 8, Suppl., 1508, 1996).

(4) Insulin sensitivity is improved after glipizide monotherapy and combination with metformin, Cefalu et al, Diabetologia, (39, Suppl. 1, A231, 1996).

(5) Combined Metformin—Sulfonyl urea Treatment of Patients with NIDDM in Fair to Poor Glycemic Control, Reaven et al, J. Clin. Endocrinol. Metab. (74, No. 5, 1020–26, 1992).

(6) Combination of Glipizide/Metformin Treatment in NIDDM, Hollenbeck et al, Diabetes, (39, Suppl. 1, 108A, 1990).

(7) Oral Antidiabetic Combination Therapy with Sulfonyl ureas and Metformin, Haupt et al, Med. Welt. (40, No. 5, 118–23, 1989).

(8) Variation of the lipemic pattern in diabetic subjects after treatment with a combination of glipizide and metformin, Ferlito et al, PROGR. MED. (Roma) 31/6 (289–301) 1975.

(9) Results with a combination of glipizide and dimethylbiguanide in 40 cases of diabetes, Parodi et al, GAZZ. MED. ITAL. 132/5 (226–235) 1973.

Other combinations of metformin and another antidiabetic agent are disclosed in the following references.

(1) U.S. Pat. No. 5,631,224 to Efendic et al discloses a combination of metformin with GLP-1(7–36) amide or GLP-1(7–37) or a fragment thereof.

(2) WO 98/57634 (SKB) discloses a method for treating diabetes employing a combination of a thiazolidenedione and metformin. The thiazolidenedione may be troglitazone, ciglitazone, pioglitazone or englitazone, and may be employed in dosages of 2 to 12 mg per day while the metformin may be employed in daily dosages "of up to 3000 mg per day, in unit doses of 500 mg (for example, 2 to 3 times per day) or 850 mg (2 times per day), one example of a dosage for metformin is 500 mg building to 5 times per day."

(3) EP 0749751A2 (Takeda) discloses a combination of a thiazolidenedione insulin sensitivity enhancer (such as pioglitazone) and metformin.

None of the above references suggests employing diabetic combinations containing metformin for first line treatment of drug naive patients.

Several fixed combinations of metformin and glyburide (glibenclamide) are presently being marketed outside the U.S. These include (1) combinations of 400 mg metformin/2.5 mg glibenclamide (Boehringer's Bi-Euglucon in Argentina, and Bi-Euglicon M in Italy; Guidotti/Menarini's Glibomet in the Dominican Republic and Italy; HMR's Normell in Greece and Hoechst's Suguan-M in Italy; Sun Pharma's Glucored in India; Monsanto's (Searle's) Benclamet in India; Guidotti's Globate in Liban; Berlin Chemie/Menarini's Glibomet in the Slovak Rep., and Roche's Bi-Euglucon in Uruguay); (2) combinations of 500 mg metformin/5 mg glibenclamide (Sun Pharma's Glucored in India; Monsanto's (Searle's) Benclamet in India, USV's Duotrol in India; and Lakeside's (Roche) Bi-Euglucon M5 in Mexico); (3) combinations of 500 mg metformin/2.5 mg glibenclamide (Molteni's Glucomide in Italy, Lakeside's (Roche) Bi-Euglucon M in Mexico and Szabo's Dublex in Uruguay); and (4) 1 g metformin/5 mg glibenclamide (Silanes Sil-Norboral in Mexico).

The labelling for Glucophage® (Bristol-Myers Squibb's metformin), in the Physicians' Desk Reference 1999, under "Indications and Use", indicates that Glucophage may be used concomitantly with a sulfonylurea. It is further indicated under "Dosage and Administration" "Concomitant Glucophage and Oral Sulfonylurea Therapy" that "If patients have not responded to four weeks of the maximum dose of Glucophage monotherapy, consideration should be given to gradual addition of an oral sulfonylurea while continuing Glucophage at the maximum dose . . . With concomitant Glucophase and sulfonylurea therapy, the desired control of blood glucose may be obtained by adjusting the dose of each drug. However, attempts should be made to identify the maximum effective dose of each drug to achieve this goal." The recommended dosing schedule for Glucophage is a starting dose of 500 mg twice a day or 850 mg once a day with dosage increases in increments of 500 mg weekly or 850 mg every 2 weeks up to a total of 2000 mg per day.

Package inserts for Bi-Euglucon M and Suguan M in Italy (400 mg metformin/2.5 mg glibenclamide) indicate that these drug combinations are used in cases of primary or secondary resistance to sulfonyl ureas [that is as second or third line therapy] and that a dosage of ½ tablet per day increasing ½ tablet at a time according to glycemic variations up to 4 tablets per day are employed.

Package inserts for Glibomet (400 mg metformin/2.5 mg glibenclamide) and Glucomide (500 mg metformin/2.5 mg glibenclamide) in Italy indicate that these drug combinations are used for treating type 2 diabetes which is non-controllable or cannot be controlled with only diet or with diet and sulfonyl urea [that is as first line therapy of second line therapy].

The package insert for Glibomet in Italy indicates a daily dosage of 2 tablets, that is 800 mg metformin and 5 mg glibenclamide, up to 2 grams metformin. The package insert for Glucomide in Italy indicates a daily dosage of 2 capsules, that is 1000 mg metformin up to 2 grams metformin, and 5 mg glibenclamide.

DESCRIPTION OF THE INVENTION

In accordance with the present invention, a low dose pharmaceutical formulation is provided which includes a combination of metformin and at least one other antidiabetic agent, which preferably is glyburide, which combination provides at least substantially equivalent efficacy in treating diabetes in drug naive patients (in first line therapy) as do combinations of metformin and the other antidiabetic agent employed in substantially higher dosages as prescribed in generally accepted medical practice for first line therapy in treating diabetes. However, use of the low dose pharmaceutical formulation of the invention results in substantially reduced side effects as compared to the same combination employed in the higher doses as generally prescribed.

It is to be understood that the low dose formulation of the invention will include a "low dose" of at least one of the active antidiabetes drug components, that is a lower dosage than the dosage for such drug prescribed in generally accepted medical practice in first line therapy of treating diabetes. Thus, the above low dose pharmaceutical formulation will include a low dose of metformin as defined hereinafter, or a low dose of other antidiabetic agent as defined hereinafter, or a low dose of each of metformin and other antidiabetic agent as defined hereinafter.

In accordance with the present invention, efficacy in first line therapy in treating diabetes in drug naive patients is achieved employing the low dose pharmaceutical formulation of the invention wherein the daily dosage of the metformin may be employed in a daily dosage prescribed in generally accepted medical practice for first line therapy in treating diabetes, and is preferably within the range which comprises a starting daily dosage as low as about one-fifth of the starting daily dosage of metformin employed in generally accepted medical practice for first line therapy for treating diabetes, up to a daily maintenance dosage of about two-thirds of the daily maintenance dosage of metformin employed in generally accepted medical practice for first line therapy for treating diabetes.

The low dose pharmaceutical formulation of the invention will more preferably contain metformin where the daily dosage of the metformin is within the range which comprises a starting daily dosage as low as about 25% up to about 60% of the starting daily dosage of metformin employed in generally accepted medical practice for first line therapy for treating diabetes, up to a daily maintenance dosage of from about 40 to about 60% of the maintenance dosage employed in generally accepted medical practice for first line therapy for treating diabetes.

Thus, in effect, the low dose pharmaceutical formulation of the invention will be employed in first line therapy in a daily dosage to provide less than about 800 mg metformin per day, preferably no more than about 750 mg metformin per day, more preferably no more than about 600 mg metformin per day, and a minimum (starting dosage) of about 160 to about 225 mg per day, in single or divided doses of one to four tablets daily.

The other antidiabetic agent (which preferably is a sulfonyl urea, preferably glyburide) may be employed in a daily dosage prescribed in generally accepted medical practice for first line therapy in treating diabetes, and is preferably employed in a daily dosage within the range which comprises a starting daily dosage as low as about one-tenth of the starting daily dosage of other antidiabetic agent employed in generally accepted medical practice for first line therapy for treating diabetes, up to a daily maintenance dosage of about two-thirds of the daily maintenance dosage of other antidiabetic agent employed in generally accepted medical practice for first line therapy for treating diabetes.

The other antidiabetic agent will preferably be employed in a daily dosage within the range which comprises a starting daily dosage as low as about 20% up to about 60% of the starting daily dosage of such other antidiabetic agent employed in generally accepted medical practice for first line therapy for treating diabetes, up to a daily maintenance dosage of about 40 to about 60% of the daily maintenance dosage of such other antidiabetic agent employed in generally accepted medical practice for first line therapy for treating diabetes.

The above daily dosage of the other antidiabetic agnet (which preferably is glyburide) includes starting daily dosages of such antidiabetic agent (for example 0.1 to 1.5 mg glyburide) up to a maximum maintenance daily dosage as prescribed in generally accepted medical practice for first line therapy in treating diabetes. In the case of glyburide, the daily dosage will preferably be up to two-thirds the daily dosage as prescribed in generally accepted medical practice for first line therapy in treating diabetes that is up to about 4.5 mg, preferably up to about 3.75 mg glyburide, per day, in single or divided doses of one to four tablets daily.

The term "low dose combination", "low dose formulation" or "low dose pharmaceutical formulation" as employed herein, in a preferred formulation of the invention, refers to a formulation which includes metformin in a starting daily dosage of as low as about one-fifth the starting daily dosage of metformin prescribed in generally accepted medical practice for first line therapy in treating diabetes up to about two-thirds the maintenance daily dosage of metformin prescribed in generally accepted medical practice for first line therapy in treating diabetes. The above daily dosage of metformin incudes starting daily dosages of metformin (for example as low as 160 mg) and dosages of metformin titrated up to a maximum maintenance dosage of less than about 800 mg metformin per day, preferably less than about 750 mg per day; and other antidiabetic agent employed in amounts set out herein.

Until now, combinations of metformin and another antidiabetic drug, for example, a sulfonyl urea, such as glyburide, have normally been used with few exceptions, as second line therapy in treating type 2 diabetes. Generally accepted medical practice daily dosages for such second line therapy employing fixed combinations of metformin and glyburide range from 3 to 4 tablets containing 400 to 500 mg metformin and 2 to 2.5 mg glyburide, or about 1200 to 2000 mg metformin and 6 to 10 mg glyburide, daily.

As indicated above with respect to Glibomet and Glucomide (fixed combinations of metformin and glyburide) marketed in Italy, these combinations may be employed as first line therapy (drug naive patients) in a daily dosage of 800 to 1000 mg up to 2 grams metformin and 5 mg glibenclamide (glyburide). This daily dosage is referred to herein as "dosages prescribed in generally accepted medical practice for first line therapy in treating diabetes" or as dosages of "prior art combinations" or "prior art daily dosages."

The above dosages may be included within the term "dosages as prescribed in generally accepted medical practice for first line therapy in treating diabetes."

As indicated above with respect to Boehringer's Bi-Euglucon M and Hoechst's Suguan M (fixed combinations of metformin and glibenclamide) marketed in Italy, these combinations are employed as second line therapy in a daily dosage starting at ½ tablet, that is, 200 mg metformin and 1.25 mg glibenclamide. The initial or starting low doses are employed to determine if the patient can tolerate the drugs and these doses are gradually titrated upwardly ½ tablet at a time up to 4 tablets per day until an efficacious dosage is achieved. The initial or starting daily dosage of ½ tablet or 200 mg metformin and 1.25 mg glibenclamide is not considered by Boehringer and Hoechst and physicians prescribing these drugs as "dosages as prescribed in generally accepted medical practice for treating diabetes."

Surprisingly, it has been found that use of the combination of metformin and glyburide in accordance with the present invention affords the following benefits. The low dose metformin is an insulin sensitizer and decreases insulin resistance at the liver, muscle and pancreas. The low dose metformin-glyburide combination acts on the pancreas as a glucose sensitizer; it decreases glucose toxicity at the pancreas and improves function of the pancreas.

In addition, in accordance with the present invention, a method is provided for treating diabetes, especially type 2 diabetes, in a drug naive human patient, which includes the step of administering to a drug naive human patient in need of treatment, as first line therapy, a therapeutically effective low dose pharmaceutical formulation of the invention which includes a combination of metformin and at least one other antidiabetic agent (preferably glyburide), in dosages as described herein, which combination provides at least substantially equivalent efficacy in treating diabetes in drug naive patients as do combinations of metformin and said other antidiabetic agent employed in dosages prescribed in generally accepted medical practice for first line therapy treating diabetes, but with substantially reduced side effects.

In addition, in accordance with the present invention, a method is provided for decreasing fasting plasma glucose, decreasing insulin resistance, decreasing hemoglobin A1c, increasing post-prandial insulin and/or decreasing post-prandial glucose excursion in a human diabetic patient, which includes the step of administering to a human patient the low dose pharmaceutical formulation of the invention which includes a combination of metformin/other antidiabetic agent, preferably glyburide. It is preferred that the low dose pharmaceutical formulation be administered as first line therapy and that the human patient be a drug naive patient.

In carrying out the method of the invention employing the preferred low dose pharmaceutical formulation of the invention containing metformin and glyburide, to treat drug naive patients for diabetes, it has been found that the efficacy in treating drug naive patients is at least substantially equivalent and incidence of side effects (gastrointestinal side effects and hypoglycemia) is surprisingly significantly and substantially reduced as compared to patients on prior art daily dosages of metformin and glyburide (that is in dosages prescribed in generally accepted medical practice for treating diabetes). Thus, while efficacy in treating drug naive patients as measured by decrease in hemoglobin $A_{1c}$ from baseline over time, decrease in fasting plasma glucose (FPG), increase in post-prandial insulin levels, and decrease in post-prandial glucose (PPG) excursion, are essentially substantially equivalent in the above-described patients when employing the low dose pharmaceutical formulation of the invention and the prior art daily dosages or prior art combinations, incidence of hypoglycemia in drug naive patients treated with prior art daily dosages is more than 3 times greater than in patients treated with the low dose pharmaceutical formulation of the invention, and incidence of gastrointestinal side effects in drug naive patients treated with prior art daily dosages is more than 20% greater than patients treated with the low dose pharmaceutical formulation of the invention.

Preferred daily dosages of a combination of metformin and glyburide will be in the range from about 175 to about 600 mg metformin, more preferably from about 200 to about 500 mg metformin, still more preferably from about 250 to about 400 mg metformin, and from about 0.5 to about 4.5 mg glyburide, preferably from about 0.625 to about 3.75 mg glyburide, and more preferably from about 1 to about 1.5 mg glyburide.

DETAILED DESCRIPTION OF THE INVENTION

The term "diabetes" as employed herein, refers to type 2 (or Type II) diabetes or non-insulin dependent diabetes mellitus (NIDDM).

The term "metformin" as employed herein refers to metformin or a pharmaceutically acceptable salt thereof such as the hydrochloride salt, the metformin (2:1) fumarate salt, and the metformin (2:1) succinate salt as disclosed in U.S. application Ser. No. 09/262,526 filed Mar. 4, 1999, the hydrobromide salt, the p-chlorophenoxy acetate or the embonate, and other known metformin salts of mono and dibasic carboxylic acids including those disclosed in U.S. Pat. No. 3,174,901, all of which salts are collectively referred to as metformin. It is preferred that the metformin employed herein be the metformin hydrochloride salt, namely, that marketed as Glucophage® (trademark of Bristol-Myers Squibb Company).

The term "substantially reduced side effects" as employed herein refers to reduced incidence of hypoglycemia and gastrointestinal adverse events including diarrhea, nausea/vomiting and/or abdominal pain, occurring with use of the low dose pharmaceutical formulation of the invention in drug naive patients as compared to patients on the same active components in the pharmaceutical formulation of the invention but at higher dosages as prescribed in generally accepted medical practice for treating diabetes.

The term "at least substantially equivalent efficacy" in treating type 2 diabetes as employed herein refers to the effectiveness of the low dose pharmaceutical formulation of the invention in treating drug naive patients to reduce and/or maintain hemoglobin $A_{1c}$ (glycosylated hemoglobin) at 7% or less, to decrease insulin resistance (by increasing post-prandial insulin level) and/or to decrease post-prandial glucose (PPG) excursion, as compared to patients treated with the same active components in the pharmaceutical formulation of the invention but at higher dosages as prescribed in generally accepted medical practice for treating diabetes.

The term "post-prandial excursion" as employed herein refers to the difference between post-prandial glucose (PPG) and fasting plasma glucose (FPG).

The low dose pharmaceutical formulation of the invention will contain metformin used in combination with another antidiabetic agent (also referred to herein as "another antihyperglycemic agent") which may be administered orally in the same dosage form or in separate oral dosage forms or by injection.

The other antidiabetic agent may be one or more of the following: a sulfonyl urea, a glucosidase inhibitor, a thiazolidinedione, an insulin sensitizer, a glucagon-like peptide-1 (GLP-1), insulin, a PPAR $\alpha/\gamma$ dual agonist, a meglitinide, and/or an aP2 inhibitor.

It is believed that the use of metformin in combination with another antidiabetic agent in accordance with the present invention produces antihyperglycemic results greater than that possible from each of these medicaments alone and greater than the combined additive antihyperglycemic effects produced by these medicaments.

The other antidiabetic agent will preferably be a sulfonyl urea such as glyburide (also known as glibenclamide), glimepiride (disclosed in U.S. Pat. No. 4,379,785), glipyride, glipizide, gliclazide or chlorpropamide, and/or other known sulfonyl ureas or other antihyperglycemic agents which act on the ATP-dependent channel of the β-cells, with glyburide being most preferred. The sulfonyl urea may be administered in the same oral dosage form with metformin or a separate oral dosage form.

Metformin will be employed in a weight ratio to the sulfonyl urea in the range from about 1000:1 to about 10:1, preferably from about 400:1 to about 100:1, more preferably from about 250:1 to about 150:1, and optimally about 200:1.

The oral antidiabetic agent may also be a glucosidase inhibitor such as acarbose (disclosed in U.S. Pat. No. 4,904,769), vaglibose, miglitol (disclosed in U.S. Pat. No. 4,639,436), which may be administered in a separate oral dosage form or the same dosage form with metformin.

Metformin will be employed in a weight ratio to the glucosidase inhibitor within the range from about 0.01:1 to about 100:1, preferably from about 0.5:1 to about 50:1.

The other antidiabetic agent may be a meglitinide, for example, repaglinide (Prondin®, NovoNordisk) or nataglinide (Starlex®, Novartis), which may be administered in a separate oral dosage form or the same oral dosage form with metformin.

Metformin will be employed in a weight ratio to the meglitinide within the range of from about 0.01 to about 500:1, preferably from about 0.5:1 to about 300:1.

Metformin may be employed in combination with a thiazolidinedione oral antidiabetic agent or other insulin sensitizers (which has an insulin sensitivity effect in NIDDM patients) such as troglitazone (Warner-Labert's Rezulin®, disclosed in U.S. Pat. No. 4,572,912), rosiglitazone (SKB-Avandia®), pioglitazone (Takeda-Lilly-Actos®), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer), which may be administered in a separate oral dosage form or the same oral dosage form with metformin.

Metformin will be employed in a weight ratio to the thiazolidinedione in an amount within the range from about 0.01:1 to about 100:1, preferably from about 0.5:1 to about 5:1.

The thiazolidinedione in amounts of less than about 150 mg oral antidiabetic agent may be incorporated in a single tablet with metformin.

The other antidiabetic agent may be an aP2 inhibitor such as disclosed in U.S. Provisional Applications No. 60/100, 677 filed Sep. 17, 1998, and No. 60/127,745 filed Apr. 5, 1999, the disclosures of which are incorporated herein by reference. Doses employed are as set out in the above applications.

Metformin will be employed in a weight ratio to the aP2 inhibitor in an amount within the range from about 0.01:1 to about 100:1, preferably from about 0.5:1 to about 2:1. The aP2 inhibitor and metformin may be incorporated in the same or separate dosage forms.

Metformin may also be employed in combination with a non-oral antihyperglycemic agent such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference), which may be administered via injection, or by transdermal or buccal devices.

Where present, the sulfonyl urea, such as glyburide, glimepiride, glipyride, glipizide, chlorpropamide or gliclazide, the thiazolidenedione, such as troglitazone, rosiglitazone or pioglitazone, the glucosidase inhibitor acarbose or miglitol, the meglitinide such as repaglinide or nataglinide, or insulin may be employed in formulations as described above and in formulations, amounts and dosing as indicated in the Physicians' Desk Reference.

Where present, GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

Metformin may be employed in combination with another antidiabetic agent which may be a PPAR α/γ dual agonist such as an N-benzyldioxothiazolidylbenzamide derivative such as disclosed in WO 96/38428 such as 5-(2,4-dioxothiazolidin-5-ylmethyl)-2-methoxy-N-[4-(trifluoromethyl)benzyl]benzamide (KRP-297), WO 98/05531 (Ligand Pharmaceuticals, Inc.) which discloses 2-(4-[2,4-difluorophenyl]-1-heptylureido)ethyl]phenoxy)-2methylbutyric acid, and WO 97/25042 and WO96/04260 (SKB) which disclose benzoxazole and pyridine derivatives of the structure

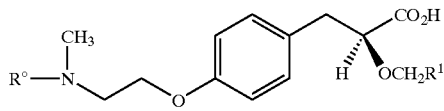

or a pharmaceutically acceptable salt thereof, and/or a pharmaceutically acceptable solvate thereof, wherein $R^0$ represents 2-benzoxazolyl or 2-pyridyl and $R^1$ represents $CH_2OCH_3$ or $CF_3$, such as (S) -3-[4-[2-[N-(2-benzoxazolyl)-N-methylamino)ethoxy]phenyl]-2-(2-methoxy-ethoxy) propanoic acid; or (S)-3-[4-[2-[N-(2-benzoxazolyl)-N-methylamino]-ethoxy]phenyl]-2-(2,2,2-trifluoroethoxy) propanoic acid; or a pharmaceutically acceptable salt thereof, and/or a pharmaceutically acceptable solvate thereof. Dosages employed are as set out in the above references.

Metformin will be employed in a weight ratio to the PPAR α/γ dual agonist within the range from about 0.01:1 to about 100:1, preferably from about 0.5:1 to about 5:1.

Where metformin is employed in combination with the PPAR α/γ dual agonist, the combination may be employed in an oral dosage form such as a tablet or capsule as will be apparent to one skilled in the art.

Preferred are low dose combinations of metformin and glyburide and optionally an insulin sensitizer such as a glitazone, for example, rosiglitazone, pioglitazone or troglitazone.

In carrying out the present invention, a low dose pharmaceutical formulation or composition will be employed containing metformin and at least one other antidiabetic agent in association with a pharmaceutical vehicle or diluent. The low dose pharmaceutical formulation can be formulated employing conventional solid or liquid vehicles or diluents and pharmaceutical additives of a type appropriate to the mode of desired administration. The low dose pharmaceutical formulation of the invention can be administered to mammalian species including humans, monkeys, dogs, etc., by an oral route, for example, in the form of tablets, capsules, granules or powders, or it can be administered by a parenteral route in the form of injectable preparations. The dose for drug naive patients is as described above, which can be administered in a single dose or in the form of individual doses from 1–4 times per day.

The above dosage forms may also include the necessary physiologically acceptable carrier material, excipient, lubricant, buffer, antibacterial, bulking agent (such as mannitol), anti-oxidants (ascorbic acid or sodium bisulfite) or the like.

The dose administered must be carefully adjusted according to the age, weight, and condition of the patient, as well as the route of administration, dosage form and regimen, and the desired result.

The combination of the metformin or salt thereof and the other antidiabetic agent may be formulated separately or, where possible, in a single formulation employing conventional formulation procedures.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer which is applied over the outer solid phase containing particles of inner solid phase embedded therein may comprise any conventional coating formulations and will include one or more film-formers or binders, such as a hydrophilic polymer like hydroxypropylmethylcellulose , and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

The finished dosage form is either a compressed tablet or a hard gelatin capsule, preferably a tablet. The tablet may be optionally film coated. The total amount of drug per dosage unit would be such as to offer a dosage form of convenient size for patients.

Where the low dose pharmaceutical formulation of the invention includes a combination of metformin and glyburide, the formulation will be administered so as to provide from about 55 to about 500 mg metformin one to four times daily, with a minimum of about 160 mg metformin daily and a maximum of less than about 800 mg, preferably up to about 750 mg metformin daily. The glyburide will preferably be administered in an amount from about 0.5 to about 3.75 mg one to four times daily, with a maximum of up to about 4.5 mg daily.

The preferred low dose pharmaceutical formulation of the invention is comprised of metformin and glyburide and is employed as initial therapy that is as an adjunct to diet and exercise to improve glycemic control in patients with type 2 diabetes mellitus.

The ADA recommends a treatment goal of $HbA_{1c}$<7% (ADA. Diabetes Care 21 [Suppl. 1]: S23–S31, 1998) in order to reduce the risk of complications of type 2 diabetes mellitus, including coronary heart disease and microvascular complications.

Dosage of the preferred metformin-glyburide combination of the invention must be individualized on the basis of both effectiveness and tolerance. It is preferably given with meals and should be started at a low dose, with gradual dose escalation. Ideally, the response to therapy should be evaluated using $HbA_{1c}$ (glycosylated hemoglobin) which is a better indicator of long-term glycemic control than FPG alone. The therapeutic goal in all patients with type 2 diabetes mellitus should be to improve glycemic control, including FPG, postprandial glucose and $HbA_{1c}$ levels, to normal or as near normal as possible. Patients should be titrated to achieve the ADA goal of $HbA_{1c}$>7% following the dosing recommendations up to the maximum recommended dose. (ADA. Diabetes Care 21 [Suppl. 1]: S23–S32, 1998).

As initial therapy, the preferred starting dose of the metformin-glyburide combination of the invention is 250/1.25 mg once a day, given with a meal. For patients with a baseline $HbA_{1c}$>9% or a fasting glucose >200 mg/dL, a recommended starting dose of 250/1.25 mg twice daily with the morning and evening meal may be preferred. Dosage increases should preferably be made in increments of 250/1.25 mg, every 2 weeks, up to the minimum effective dose necessary to achieve adequate glycemic control. For those patients requiring additional glycemic control, the 250 mg/1.25 mg dosage may be switched to 500/2.5 mg. However, as indicated, the preferred maximum daily dosage for metformin is 600 to 750 mg and the preferred maximum daily dosage for glyburide is 3.75 mg.

The low dose pharmaceutical formulation containing the metformin-glyburide combination, in accordance with the present invention, will preferably be formulated according to the teachings disclosed in U.S. application Ser. No. 09/353,141, filed Jul. 14, 1999, which claims priority from European application No. 98401781.4 filed Jul. 15, 1998, which U.S. application is incorporated herein by reference.

The preferred low dose metformin-glyburide formulation is set out below.

| Product identity | Amount of ingredient, mg per tablet 250/1.25 |
|---|---|
| Ingredient | |
| Metformin hydrochloride | 250.0 |
| Glyburide | 1.25 |
| Croscarmellose sodium | 3.0–15.0 |
| Microcrystalline cellulose | 15.0–60.0 |
| Polyvinyl pyrrolidone | 3.0–18.0 |
| Magnesium stearate | 0.3–7.5 |
| Film coat* | 4.5–12.0 |

*a commercially available film coat composition is used, such as Opadry (Colorcon, UK).

The especially preferred low dose metformin-glyburide formulations are as follows:

| Product identity | Amount of ingredient, mg per tablet 250/1.25 |
|---|---|
| Ingredient | |
| Metformin hydrochloride | 250.0 |
| Glyburide | 1.25 |
| Croscarmellose sodium | 7.0 |
| Microcrystalline cellulose | 28.25 |
| Polyvinyl pyrrolidone | 10.0 |
| Magnesium stearate | 0.6–6.0 |
| Film coat* | 4.5–12.0 |

*a commercially available film coat composition is used, such as Opadry (Colorcon, UK).

The low dose pharmaceutical formulation of the invention in the form of a solid oral form such as a tablet, will preferably contain a combination of metformin and glyburide in which the size of the glyburide is such that at most 10% of the particles are less than 2 µm and at most 10% of the particles are greater than 60 µm. Preferably, the size of the glyburide is such that at most 10 of the particles are less than 3 µm and at most 10% of the particles are greater than 40 µm. This specific size range of glyburide may be obtained by sieving or air jet milling.

In a second embodiment, the low dose solid oral dosage form of the invention will contain a combination of metformin and glyburide in which the size of glyburide is such that at most 25% of the particles are less than 11 µm and at most 25% of the particles are greater than 46 µm.

Preferably, 50% of particles are less than 23 µm.

Most preferred are a combination of metformin and glyburide, where the glyburide has a particle size distribution of about 25% undersize value not more than 6 µm, about 50% undersize value 7 to 10 µm and about 75% undersize value not more than 23 µm.

The low dose pharmaceutical formulation of the invention in the form of a tablet may be obtained by a process which includes the steps of a) forming granules by wet granulation of a mixture of metformin and glyburide b) blending the granules with a tabletting aid and diluent, and c) tabletting the blend thus obtained into tablets.

The mixture used for forming the granules includes a granulating binder. The granulating binder is preferably a polyvinylpyrrolidone such as, for example, a polyvinylpyrrolidone having a molecular weight of 45,000. The polyvinylpyrrolidone may be used in a proportion of 2 to 4% by weight with respect to the final tablet.

After the granulating step, the granules may be sieved and dried.

The granules are then blended with a diluent and tabletting aid. The diluent may be a conventional filler usually used for making tablets, such as microcrystalline cellulose. The tabletting aid may be a conventional material, such as magnesium stearate.

The tablets thus obtained may then optionally be coated with a hydrophilic cellulose polymer and talc. The hydrophilic cellulose polymer is preferably 2-hydroxypropyl methylcellulose.

Figure 1:
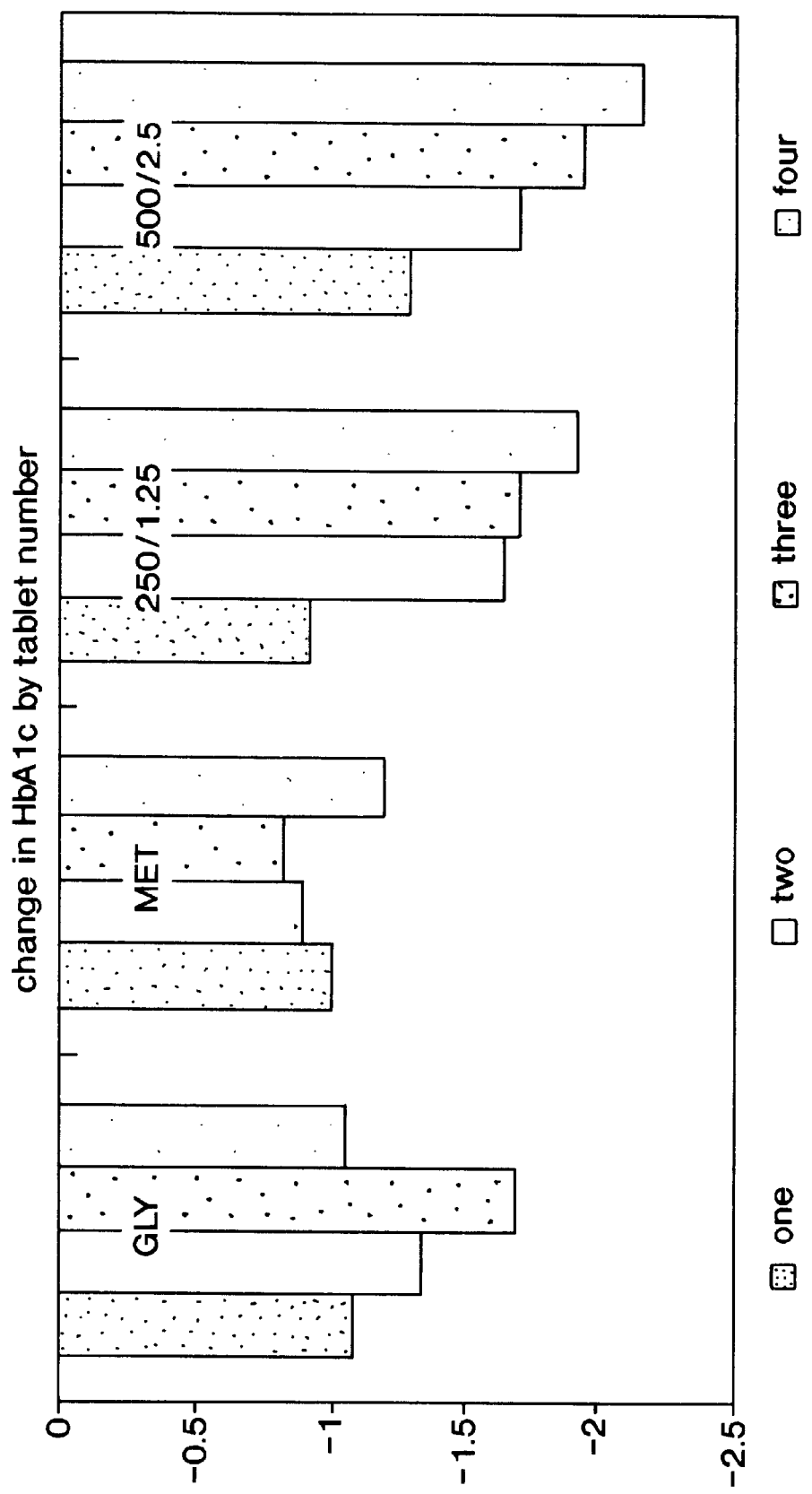
FIGS. 1 and 2 are bar graphs which depict change in hemoglobin A1c (HbA1c) by number of tablets of fixed combinations of metformin/glyburide used in first line therapy versus monotherapy with each of glyburide and metformin.

The following Examples represent preferred embodiments of the invention.

EXAMPLES 1 and 2

Tablets containing metformin/glyburide combinations were prepared as described below.

| Composition of Metformin Hydrochloride-Glyburide Tablets 250 mg/1.25 mg and 500 mg/2.5 mg | | |
|---|---|---|
| | Example 1 | Example 2 |
| | QUANTITY PER TABLET (mg) | |
| INGREDIENT | 250 mg/1.25 mg | 500 mg/2.5 mg |
| Metformin Hydrochloride | 250.0 | 500.0 |
| Glyburide | 1.25 | 2.5 |
| Croscarmellose Sodium | 7.00 | 14.0 |
| Povidone | 10.00 | 20.0 |
| Microcrystalline Cellulose | 28.25 | 56.5 |
| Magnesium Stearate | 2.25 | 4.5 |
| Film Coat* | 6 | 12 |

*HPMC based film coat used.

The metformin hydrochloride-glyburide tablet products, 250 mg/1.25 mg and 500 mg/2.5 mg, were compressed from the same granulation. The lower strength tablet was compressed at half the weight of the metformin hydrochloride-glyburide 500 mg/2.5 mg tablet. Tablets manufactured for clinical use were film-coated with a hydroxypropylmethylcellulose (HPMC) film coat. The film coat was non-functional and was applied for aesthetic purposes. The film coat applied to the clinical product was clear.

The manufacturing process for clinical products proceeded as follows:

Croscarmellose sodium and glyburide were dispersed together followed by blending with the metformin hydrochloride/magnesium stearate (99.5%:0.5% w/w) in a high shear mixer. The resultant dry mix was granulated in a high shear mixer with an aqueous povidone solution and dried in a fluid bed dryer at approximately 60° C. to achieve a specified moisture content, determined by loss on drying. The dried granulation was reduced with a screening mill and mixed with the microcrystalline cellulose using a tumble mixer. Magnesium Stearate was incorporated as a lubricant using a tumble mixer to produce the final compression blend.

The resultant blend was compressed into tablets, to a target weight that was adjusted based on in-process moisture content determinations, on a suitable tablet press. The theoretical tablet weight (based on formula composition with no adjustment for moisture content) was 300 mg for the 250 mg/1.25 mg strength and 600 mg for the 500/2.5 mg strength products.

The tablets were film-coated in a perforated coating pan with an appropriate aqueous non-functional HPMC based film coating system until the required amount of film coat had been applied. The typical level of film coat applied to the tablets was 2% w/w.

In vivo evaluations of prototype combination tablet formulations identified the particle size distribution targeted for use in the clinical program to achieve comparable bioavailability to Micronase from the combination product. The particle size distribution of any glyburide lot was described by three cumulative size criteria: 25% undersize, 50% undersize (also known as the mass median particle size, MMPS) and 75% undersize values. The clinical program involved a total of six glyburide drug substance lots with the 25% undersize value ranging between 4–7 $\mu$m, the 50% undersize value ranging between 8–14 $\mu$m and the 75% undersize value ranging between 17–26 μm. All six lots of glyburide were synthersized by the same vendor, Profarmaco, with four of them being micronised by Profarmaco. The particle size distributions of the four lots produced are detailed in the following table.

Particle Size Data for Glyburide Drug Substance Batches Used In Clinical Program

| Batch Number | Particle Size[A] (units are equivalent sphere diameters in μm) | | |
|---|---|---|---|
| | 25% Undersize | 50% Undersize | 75% Undersize |
| 1 | 5 | 9 | 21 |
| 2 | 5 | 9 | 21 |
| 3 | 4 | 8 | 18 |
| 4 | 5 | 9 | 18 |

[A]Particle size measured by laser light scattering, method reference #CRM 8532 (#SM 248533)

The proposed particle size specification included the three cumulative size criteria described above with a range for acceptable mass median particle size (50% undersize) and an upper limit for the lower quartile (25% undersize), and the upper quartile (75% undersize). The particle size specification established for glyburide had been based on the particle size of glyburide used in bioavailability studies, the experience of various clinical lots, the closely matching nature of the size distributions of commercially produced glyburide and the particle size method precision. The particle size criteria described below assured reproducibility of glyburide dissolution and bioavailability from metformin hydrochloride-glyburide tablets.

25% undersize value not more than 6 μm
50% undersize value 7–10 μm
75% undersize value not more than 23 μm

EXAMPLE 3

A. Summary of 5 Clinical Protocols (1) Purpose

The following study was conducted to compare glycemic control of 2 dosage strengths of a fixed combination metformin/glyburide product (described in Examples 1 and 2) versus placebo in drug naive patients with type 2 diabetes mellitus who have had inadequate glycemic control with diet and exercise. The dosage strengths of fixed combination product evaluated included metformin 250 mg with glyburide 1.25 mg, and metformin 500 mg with glyburide 2.5 mg. Glycemic control was assessed using Hemoglobin A1c ($HbA_{1c}$), the gold-standard measure of long-term glycemic control. Mean change from baseline in $HbA_{1c}$ following a 20 week treatment period (4 weeks stable once daily dose, 4 week titration and 12 weeks stable dose) were compared. The treatment phase continued for an additional 12 weeks to assess durability of efficacy.

Contribution of the individual components of the fixed combination product were assessed by comparison of short term glycemic parameters of the combination product and monotherapy arms after 4 weeks of stable once daily dosing. Glycemic control was achieved with similar incidence of hypoglycemia with the fixed dose combinations as compared with sulfonyl urea alone or trends towards decreased gastrointestinal side effects as compared with metformin alone. Glycemic control was achieved with trends toward decreased adverse events as compared with either agent alone. Trends in hypoglycemia, gastrointestinal symptoms and lactate levels were assessed.

(2) Study Sites and Subject Population

Eligible subjects were drug naive or have had no oral antihyperglycemic therapy for the 2 months prior to screening. Approximately 100 study sites located in the USA were recruited up to a maximum of approximately 800 subjects. Eligible subjects included both males and females between 30 and 78 years of age with established type 2 diabetes mellitus, history of impaired glucose tolerance or impaired fasting glucose who have inadequate glycemic control with diet and exercise.

(3) Study Design and Duration

This study was a 34 week, multicenter, randomized, placebo-controlled, double-blind, parallel study with an optional long-term, open-label treatment phase.

(4) Outcome Measures

Analysis of outcome measures for Periods B and C was performed after all data was made available from the 32 week randomized treatment period.

The primary outcome variable for efficacy was the change from baseline in $HbA_{1c}$ of the two combination therapies relative to placebo following 20 weeks of randomized treatment.

Secondary outcomes included the following:

Incidence of adverse events, particularly hypoglycemia and gastrointestinal side effects, was compared among treatment arms after 20 and 32 weeks of randomized therapy.

The number and proportion of subjects achieving a therapeutic glucose response were assessed among treatment arms following 20 and 32 weeks of randomized therapy.

The reduction in fasting and 2-hour postprandial glucose and insulin were assessed among treatment arms following 20 and 32 weeks of randomized therapy.

B. Rationale

Metformin and sulfonyl ureas, such as glyburide, are a known and effective combination in the treatment of type 2 diabetes mellitus. The two drugs have demonstrated a synergistic effect on glucose lowering when used in combination. Either drug can be used alone as first line monotherapy. They may also be used in combination with each other if monotherapy of either is inadequate. No data currently exists on the use of low dose combination therapy for first line use.

Treatment with a fixed dose combination tablet was expected to improve glycemic control as first line therapy in subjects with type 2 diabetes mellitus with inadequate control on diet and exercise. Glycemic control was expected to be achieved at lower doses than monotherapy with comparable or less potential side effects of the individual agents and with ease of administration.

This randomized double-blind, placebo-controlled study in subjects with type 2 diabetes mellitus who have inadequate glycemic control on diet and exercise tested the following hypotheses:

1. Administration of a fixed dose metformin/glyburide combination product for 20 weeks (4 weeks stable once daily dosing in Period B and 16 weeks of treatment in Period C) in subjects with type 2 diabetes mellitus who have inadequate glycemic control on diet and exercise will produce significant reductions in $HbA_{1c}$ compared to placebo.

2. Administration of a fixed dose metformin/glyburide combination product for 32 weeks in subjects with type 2 diabetes mellitus who have inadequate glycemic control on diet and exercise will be well tolerated.

C. Objectives (1) Primary

To compare, after 20 weeks of oral administration, the effect of 2 dosage strengths (Examples 1 and 2) of a fixed combination metformin/glyburide tablet that has been titrated for glycemic control on the reduction in $HbA_{1c}$ level versus placebo.

(2) Secondary (Included the Following)

1. To assess safety and tolerability among treatment arms after 20 and 32 weeks of randomized therapy. Glycemic control may be achieved with a similar incidence in hypoglycemia with the fixed dose combinations as compared with sulfonyl urea alone or decreased gastrointestinal side effects as compared with metformin alone.
2. To assess after 20 weeks and assess after 32 weeks, the proportion of subjects with a therapeutic response in glycemic control of oral administration of each metformin/glyburide combination regimen when compared to the therapeutic response achieved with metformin monotherapy, glyburide monotherapy and placebo regimens. Therapeutic plasma glucose response will be defined as a FPG<126 mg/dL (based on current ADA guidelines for FPG). Therapeutic response for $HbA_{1c}$ will be defined as $HbA_{1c}<7\%$.
3. To assess after 20 weeks and assess after 32 weeks, the reductions in fasting glucose and 2-hour postprandial glucose and insulin levels following the oral administration of each fixed combination metformin/glyburide regimen with the reduction in fasting glucose and 2-hour postprandial glucose and insulin level achieved with metformin monotherapy, glyburide monotherapy and placebo.
4. To assess the durability of reductions in $HbA_{1c}$ levels after 32 weeks of administration of fixed combination metformin/glyburide product.
5. To assess long-term safety and efficacy of fixed combination metformin/glyburide products.

D. Study Design

This was a multicenter, randomized, five-arm, parallel group, double-blind, placebo controlled trial of the antihyperglycemic activity of a fixed combination metformin/glyburide tablet as first line therapy in subjects with type 2 diabetes mellitus who have inadequate glycemic control ($HbA_{1c}<7\%$), with diet and exercise. Patients were drug naive or had no oral antihyperglycemic therapy for the 2 months prior to screening. Approximately 100 US sites enrolled up to a maximum of 800 patients with type 2 diabetes mellitus who had inadequate glycemic control defined as an $HbA_{1c}$ between 7–11% on diet and exercise. The minimum number of patients required to achieve the primary outcome was a total of 500 patients or 100 patients per arm. However, recruitment continued for up to 6 months to recruit up to a maximum of 150 patients per arm to provide additional safety information. The design included 3 periods as follows:

(1) Period A—Two Week Dietary and Placebo

Lead-in Phase

This initial phase included dietary instruction on a eucaloric, weight maintaining diabetes prudent diet consistent with ADA guidelines or a balanced diet of approximately 55% carbohydrates, 20% protein and 25% fat. Tolerability of the administration of multiple capsules and tablets were assessed with placebo. Home glucose meters were dispensed with instruction on their use.

(2) Period B—4 Week Double-blind Once Daily Stable Dose Phase

Period B began the randomized, double-blind, parallel quadruple dummy treatment phase. Eligible patients were randomized to 1 of 5 study arms which included placebo, glyburide monotherapy, metformin monotherapy, and two different dose strengths of fixed combination metformin/glyburide product (Examples 1 and 2). Subjects were maintained on once daily dosing for a 4 week period so that the contribution of the individual components of the combination product can be assessed by short term glycemic parameters.

This 4 week phase at stable once daily dosing illustrated the contribution of the individual components of the fixed combination product using short term glycemic parameters. Glycemic control was assessed with fructosamine and fasting glucose.

(3) Period C—28 Week Double-blind Titration and Stable Dose Phase

Period C was the continuation of the randomized, double-blind treatment phase. Subjects were titrated for glycemic control over the first four weeks then dose was maintained for a 24 week stable dose treatment segment. Analysis for the primary outcome, the change from baseline in $HbA_{1c}$ of the two combination therapies (Examples 1 and 2) relative to placebo, was assessed at week 16 of Period C which was after 20 weeks of randomized, double-blind treatment. This was done at this time as there had been adequate time for stabilization of $HbA_{1c}$ and for safety reasons as it was anticipated that a high number of placebo treated patients may have had to discontinue randomized study medication due to insufficient glycemic control as treatment duration was extended. Subjects not discontinuing randomized study drug due to lack of efficacy remained on stable doses for a total of 24 weeks to evaluate durability of efficacy and gather additional safety and tolerability data. The study remained blinded and those subjects who discontinued randomized study drug due to lack of efficacy were eligible to begin the long-term, open-label treatment phase with fixed combination product.

This 28 week phase included an initial 4 week titration segment to improve glycemic control followed by a 24 week stable dose phase. Analysis for the primary outcome was assessed at the $16^{th}$ week of Period C. Subjects were evaluated for discontinuation of randomized study drug due to lack of glycemic control beginning at visit C1 through C85. Subjects were evaluated for lack of efficacy at visit C113 and all subsequent visits until the end of randomized treatment. The assignment of randomized study drug remained blinded. Subjects who remained on randomized study drug continued the stable dose phase for a total of 28 weeks to allow evaluation of durability of efficacy and to gather additional safety and tolerability data. Subjects were evaluated for discontinuation of study medication due to lack of glycemic control on or after Visit C1 (Week 0, Period C).

Dosing

Study drugs for this study were defined as: placebo, glyburide, metformin, metformin/glyburide 250/1.25 mg and metformin/glyburide 500/2.5 mg. For blinding purposes this study incorporated a quadruple-dummy design. Patients meeting the inclusion criterion without meeting any exclusion criterion, satisfying the Period A glycemic criteria, were eligible for enrollment into Period A.

Period A:

This period was a single-blind placebo lead-in to test patient tolerability of ingesting multiple capsules and tablets in addition to evaluating compliance with the quadruple dummy design. Patients received kits containing four bottles of placebo corresponding to study drug.

Week 0 (Visit A1)—Subjects were instructed to take 1 capsule or tablet from each bottle with their first meal of the morning.

Week 1 (Visit A8)—Subjects were instructed to take 1 capsule or tablet from each bottle with their first meal of the day and a second capsule or tablet from each bottle with their evening meal.

Period B:

Following completion of the single-blind lead-in phase (Period A), qualifying subjects commenced therapy in the randomized, double-blind treatment phase (Period B). At visit A15/B1 subjects were randomized to once daily dosing with breakfast of placebo, glyburide 2.5 mg, metformin 500 mg, metformin/glyburide 250/1.25 mg or metformin/glyburide 500/2.5 mg. once daily dosing remained stable for a total of 4 weeks.

Period C:

Following completion of the 4 week stable once daily dose phase (Period B) subjects continued the same randomized therapy in the 28 week titration/stable dose treatment phase (Period C). Study medication was titrated at visits Cl, C15 and C29. Medication was dosed with the first morning meal and with the evening meal. Potential maximal doses achieved included glyburide 10 mg, metformin 2000 mg, metformin/glyburide 1000/5 mg, metformin/glyburide 2000/10 mg. After the 4 week titration segment in Period C, subjects continued on a stable dose of study medication for the remainder of Period C.

Once adequate glycemic control had been achieved or maximum dose had been attained, study drug was not increased and was only reduced with documented hypoglycemia.

Results

Figure 2:
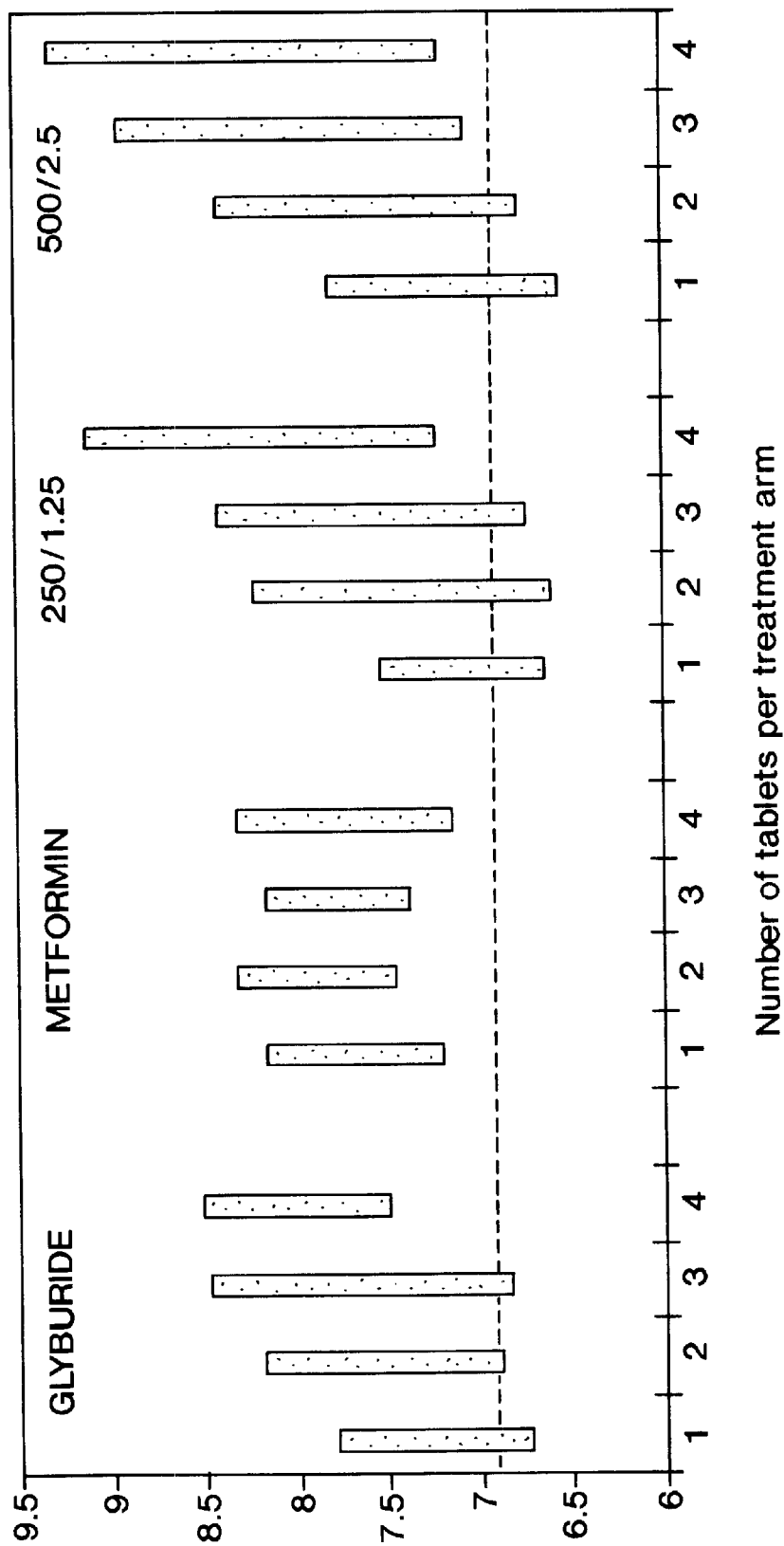
Figure 3:
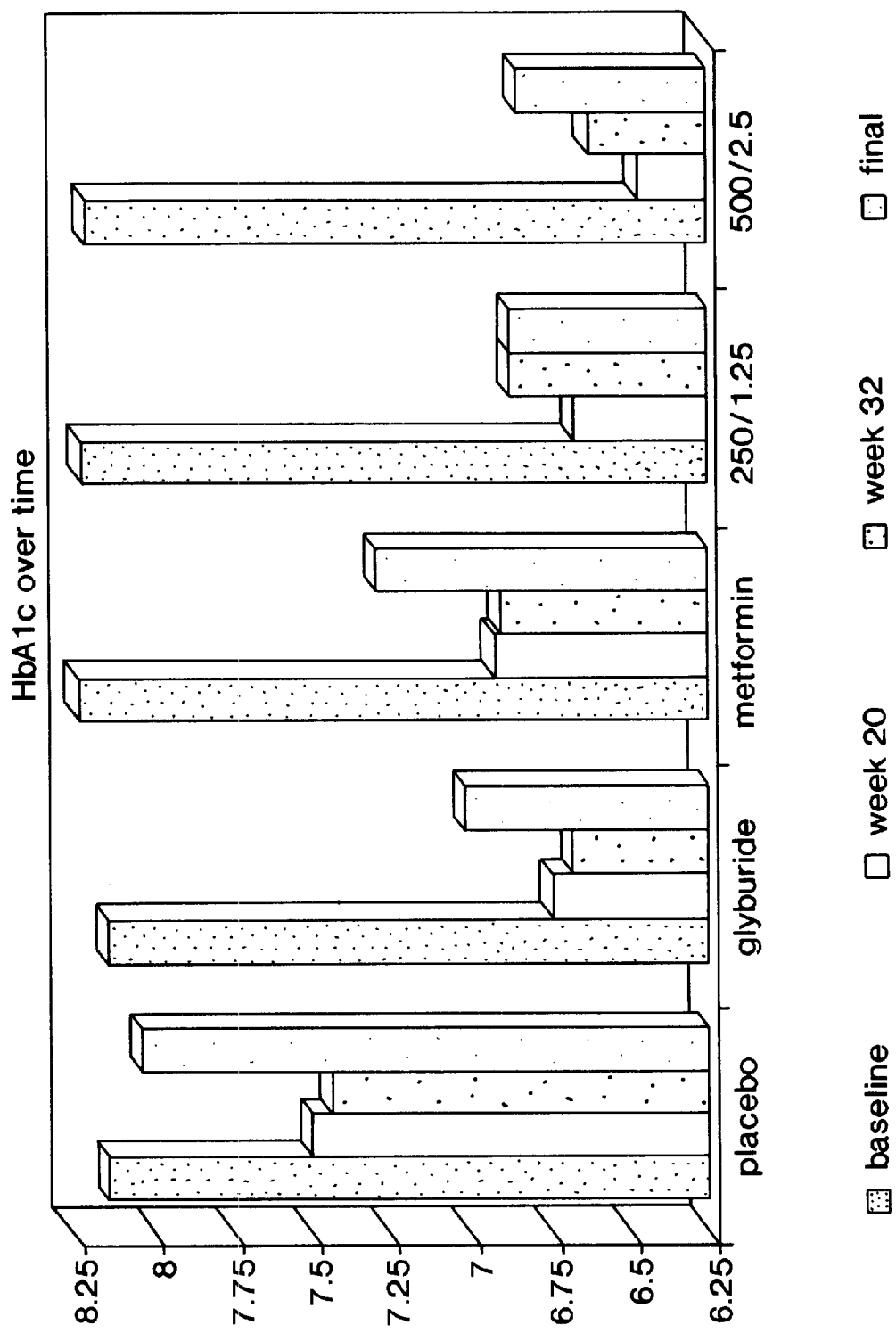
FIGS. 3, 4 and 5 are bar graphs which depict change in HbA1c over time of fixed combinations of metformin/glyburide used in first line therapy versus monotherapy with each of glyburide and metformin.
Figure 4:
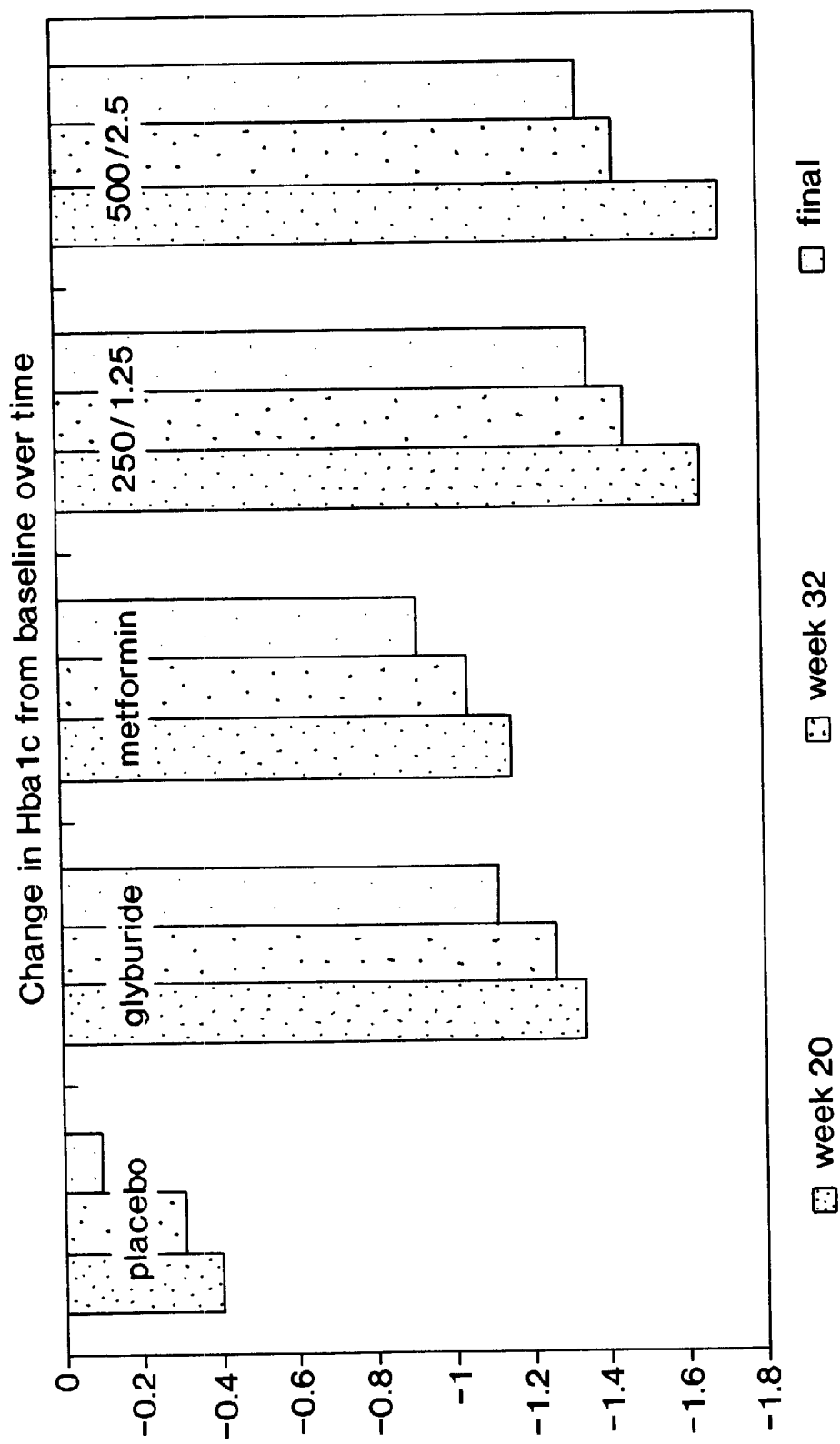
Figure 5:
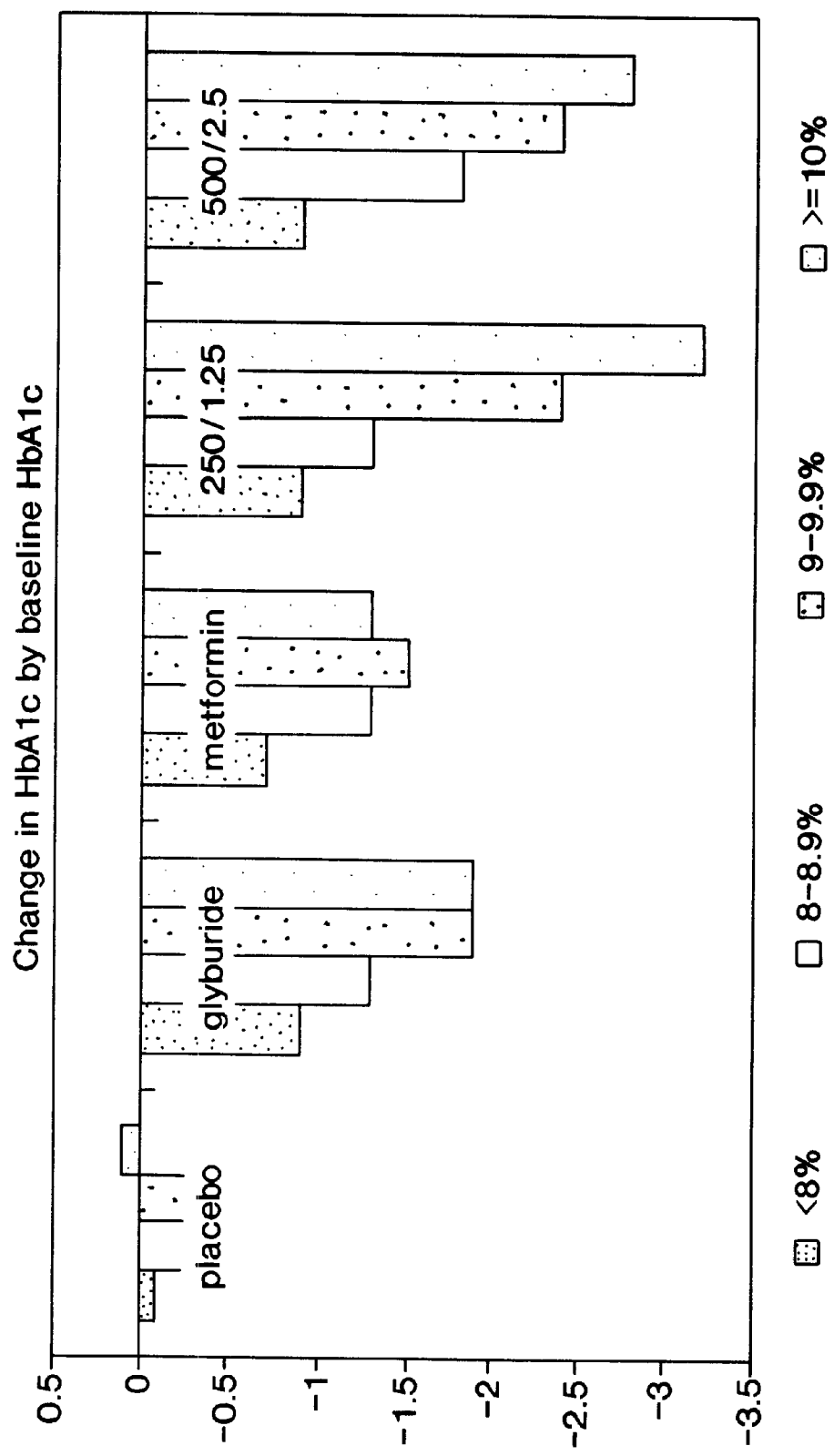

The results obtained from the above studies indicate that the low dose metformin-glyburide (250/1.25) formulation of the invention achieved glycemic control at least essentially equivalent to the high dose metformin-glyburide (500/2.5) formulation as evidenced by (1) a therapeutic response for hemoglobin A1c, namely, a reduction in HbA1c of below 7% (from a mean baseline of 8.2%) at week 20 (FIGS. 1, 2 and 3), at weeks 20 and 32 and final visit (FIGS. 4 and 5)

Figure 6:
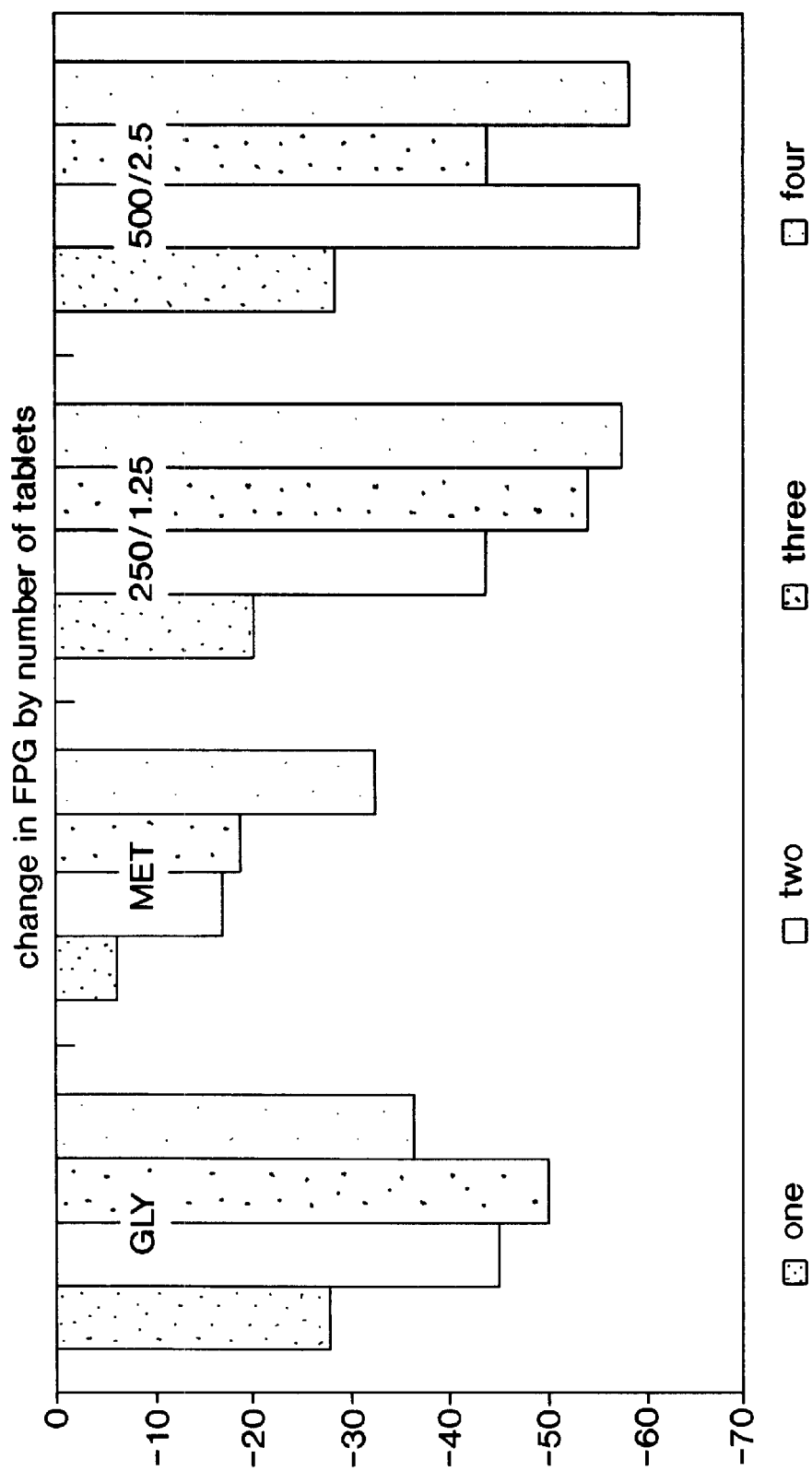
FIG. 6 is a bar graph which depicts change in fasting plasma glucose (FPG) by number of tablets of fixed combinations of metformin/glyburide used in first line therapy versus monotherapy with each of glyburide and metformin.

(2) a therapeutic response for fasting plasma glucose (FPG), namely, a reduction in FPG to less than 126 mg/dL after 20 weeks (from a baseline of about 175 mg/dL), (as shown in FIGS. 6)

Figure 7:
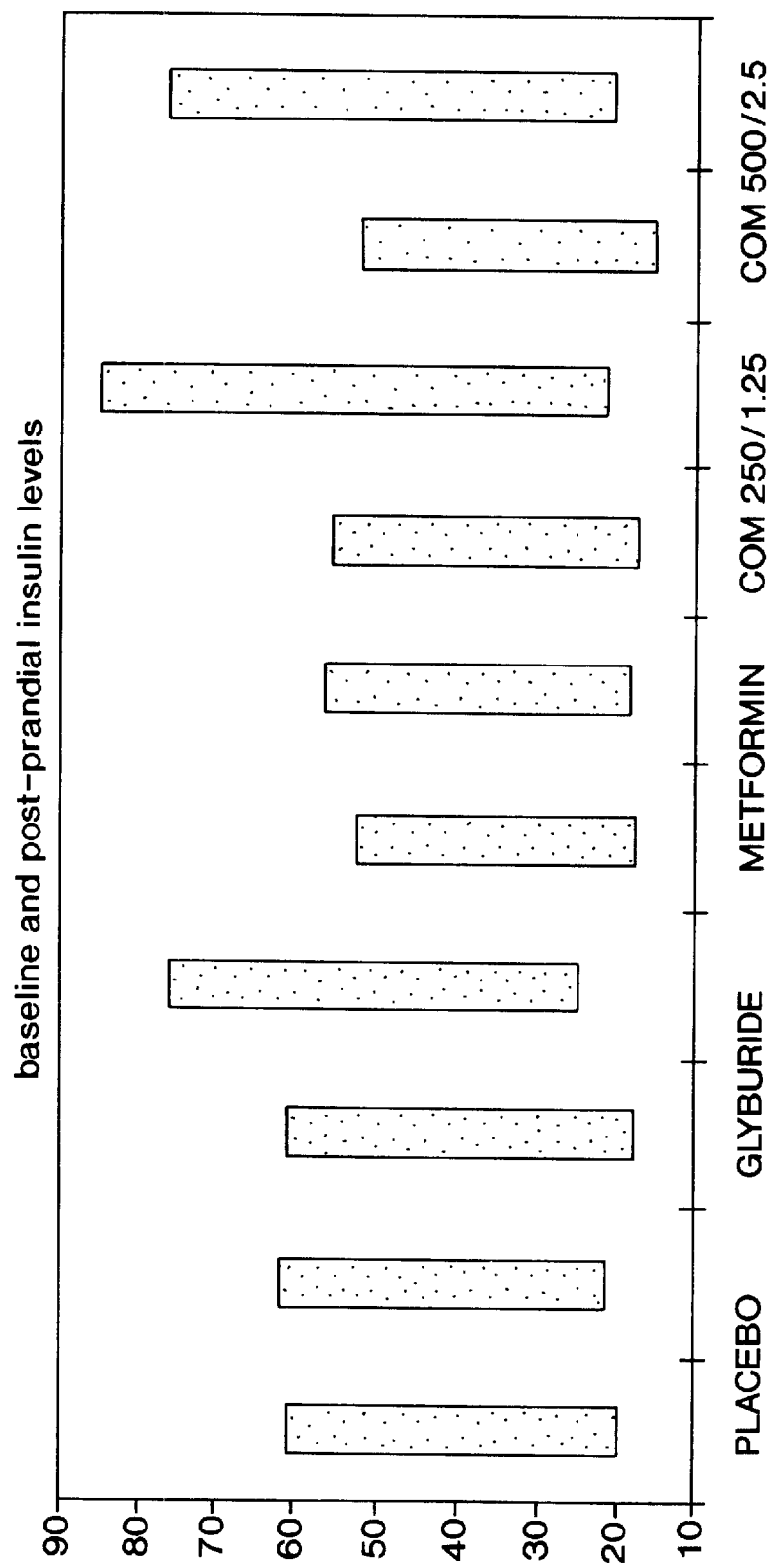
FIG. 7 is a bar graph which depicts baseline and postprandial insulin levels of fixed combinations of metformin/glyburide in first line therapy versus monotherapy with glyburide and metformin.

(3) a therapeutic response for post-prandial insulin levels, namely an increase in post-prandial insulin of 19–25 $\mu$iu/mL (microinternational units/mL) (FIG. 7)

Figure 8:
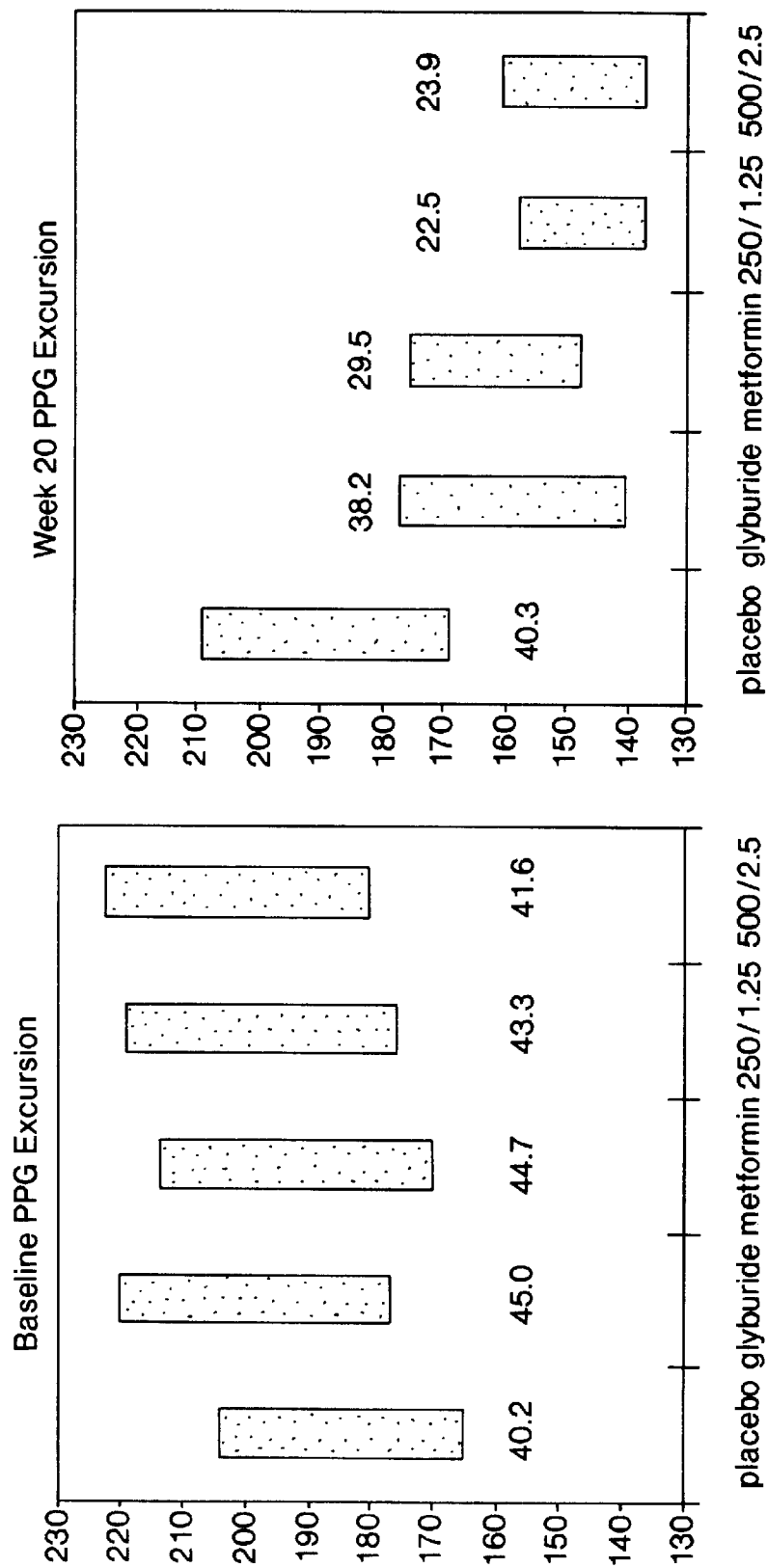
FIGS. 8A and 8B are bar graphs which depict change in PPG excursion at baseline and after 20 weeks of fixed combinations of metformin/glyburide used in first line therapy versus monotherapy with each of glyburide and metformin.

(4) a therapeutic response for post-prandial glucose excursion (PPG) (that is the difference between post-prandial glucose and fast plasma glucose), namely, a decrease in post-prandial glucose excursion at week 20 of 17.7 for the 500/2.5 mg combo and 20.8 for the 250/1.25 mg combo versus 15.2 for metformin, 6.8 for glyburide. (FIGS. 8A and 8B).

Figure 9:
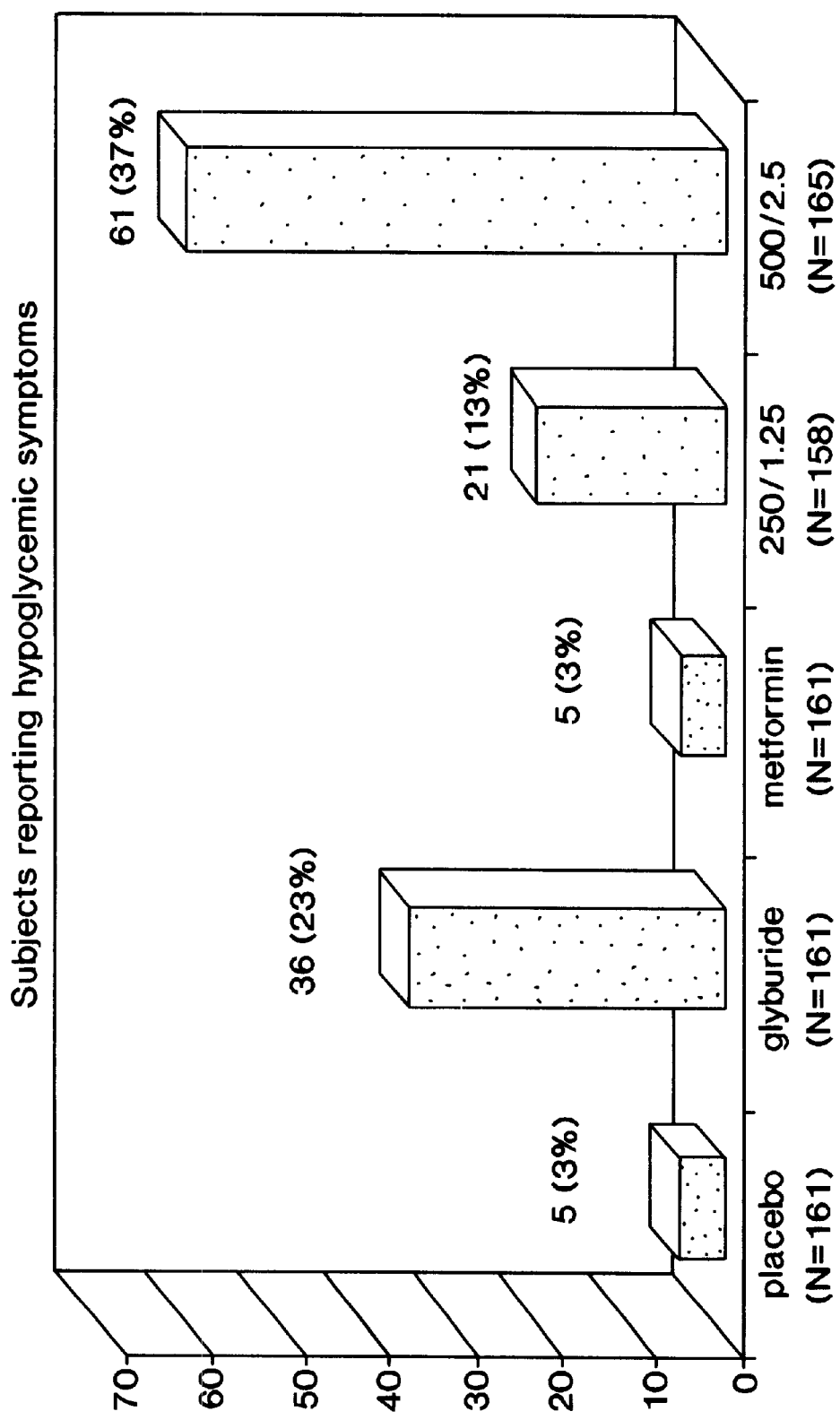
FIG. 9 is a bar graph which depicts hypoglycemic symptoms in subjects on fixed combinations of metformin/glyburide used in first line therapy versus monotherapy with each of glyburide and metformin.
Figure 10:
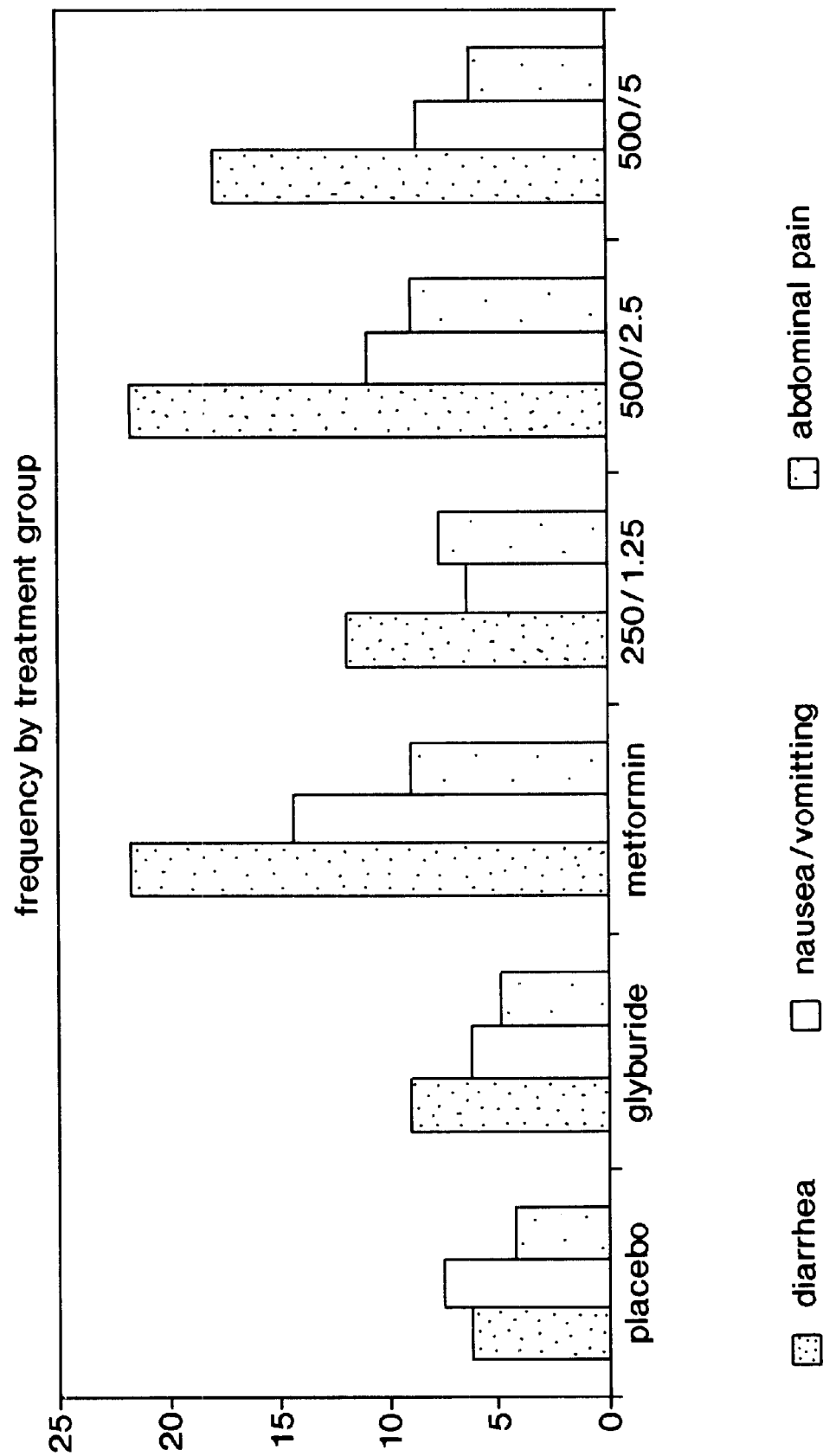
FIG. 10 is a bar graph which depicts frequency of gastrointestinal adverse effects in subjects on fixed combinations of metformin/glyburide used in first line therapy versus monotherapy with each of glyburide and metformin.

At the same time, the above efficacy results employing the low dose formulation of the invention (Example 1) were achieved with reduced incidence of side effects (FIGS. 9 and 10).

As seen in FIG. 9, the incidence of hypoglycemia employing the low dose formulation of the invention (Example 1) is less than about ⅓ of that occurring using the prior art high dose formulation (Example 2) employed in generally accepted medical practice for treating diabetes.

As seen in FIG. 10, the incidence of gastrointestinal side effects employing the low dose formulation of the invention (Example 1) is less than 20% of that occurring using the high dose formulation (Example 2) employed in generally accepted medical practice for treating diabetes.

A discussion of the above results follows.

Discussion of Results

The progression to clinical type 2 diabetes takes time and requires the presence of multiple physiologic defects which are already present by the time most individuals are diagnosed with diabetes. Oral therapeutic options for the treatment of type 2 diabetes, until the last few years, have been severely limited. Further, with continued disease progression over time, all oral antihyperglycemic therapies are expected to become less effective leading to inadequate glycemic control for the patient.

Combination therapy has traditionally been indicated for second line use if initial single agent therapy is found to be ineffective, called "primary failure," or after initially effective agents are found to be ineffective at maintaining glucose control, called "secondary failure." Switching from one monotherapy that is failing to an alternative monotherapy has not been proven to be effective in achieving glycemic control; only the addition of a second agent with a different mechanism of action has been shown to achieve improved glycemic control. Given that a combination of insulin resistance and relative deficiency of insulin secretion is the pathophysiological basis of type 2 diabetes, it is expected that combinations of agents offer greater therapeutic potential. Thus, both clinical experience and pathophysiologic evidence support the use of combination therapy earlier in the disease process.

While a fixed combination of metformin and glyburide is not a novel concept, and, as discussed above, different forms of it are available outside the U.S. for first and second line therapy, the use of combination therapy, low or moderate dose, as first line treatment in drug naive patients has never been studied in large controlled clinical trials. Treating to a near euglycemic target, an $HbA_{1c}<7\%$ as recommended by the ADA, is the goal with any antihyperglycemic therapy. However, depending upon the duration of diabetes and the progression of the disease, a single agent may not provide the efficacy necessary to bring even newly diagnosed patients to their target goal. The data presented in this summary provides evidence that a low dose fixed combination metformin/glyburide product is safe and provides the efficient antihyperglycemic potency necessary to bring most drug naive patients to the ADA's recommended glycemic target.

As first line therapy, a single formulation of fixed combination metformin/glyburide in ratio of a 200:1 metformin/glyburide was evaluated using two different dose strengths, a low dose (metformin/glyburide 250/1.25 mg) and a medium dose (metformin/glyburide 500/2.5 mg). The two dose strengths of fixed combination metformin/glyburide product were compared in a double-blind study to placebo, glyburide monotherapy and metformin monotherapy. Mean final doses achieved in each treatment arm were approximately 5.3 mg of glyburide, 1307 mg of metformin, 557/2.78 mg of low dose (250/1.25 mg) metformin/glyburide fixed combination and 818/4.1 mg of medium dose (500/2.5 mg) fixed combination. When used as first line therapy, fixed combination metformin/glyburide treatment achieved statistically significant improvement in glycemic control compared to metformin, glyburide or placebo. The interim open-label treatment data confirmed the clinical utility of fixed combination therapy in a more "glycemically diverse" patient population and for a longer period of time. Safety As first line therapy use, two dose strengths of metformin/glyburide were evaluated; a low-dose (250/1.25 mg) and a medium dose (500/2.5 mg) strength were compared with placebo, glyburide and metformin. In the double-blind phase of this study, diarrhea was the most frequently-occurring adverse effects (AE) in those subjects who were on metformin mono- or combination therapy. Importantly, however, the incidence of gastrointestinal AEs was lower in the low dose fixed combination group than in the metformin monotherapy group (as seen in FIG. 10). Discontinuations due to AEs also occurred with the lowest frequency in the low dose fixed combination group compared to any of the other active treatments. Discontinuations due to lack of glycemic control were lowest in both the fixed combination groups, and severe hypoglycemia was not observed in this study. The frequency of subjects reporting an episode of hypoglycemia was highest in the medium dose fixed combination treatment group, while the low dose group had a lower incidence than glyburide monotherapy (FIG. 9). Mild increase in lactate levels were observed in all metformin groups, but no cases of lactic acidosis were reported in this study.

In the open-label phase of the study, subjects could be directly enrolled if they did not meet the glycemic criteria for entry into the double blind study. Subjects could also enter the open-label phase if they discontinued prematurely from the double-blind phase due to lack of glycemic control, or after they completed the double-blind phase. In the open-phase of the study, the AE profile was similar to that observed in the double-blind phase, with the most frequently-occurring AEs in the same body systems. The low dose combination group again displayed a favorable overall safety profile compared to the medium dose group.

In both the newly-diagnosed subjects as well as inadequately-controlled subjects, the overall pattern of safety and tolerability observed in the double-blind studies was as expected from the clinical experience with metformin and glyburide. No new or unexpected events or laboratory abnormalities were observed in this clinical program. Interim analyses of the long-term open-label extensions support the favorable safety profile observed in the short-term phase of the studies. In particular, the low dose fixed combination showed a favorable safety/tolerability profile when compared to the other regimens used in this program.
Efficacy Double-blind, first line therapy demonstrated a statistically significant mean decrease in HemoglobinA$_{1c}$ (HbA$_{1c}$) of 1.3% from placebo for both fixed combination treatment groups and a mean decrease from baseline of approximately 1.5%. While all active therapy treatment groups achieved acceptable glycemic control, greater mean decreases in HbA$_{1c}$ for both fixed combination treatment groups were achieved when compared to metformin therapy of glyburide therapy. Antihyperglycemic durability was observed with all active treatment groups (glyburide, metformin, metformin/glyburide 250/1.25 mg, metformin/glyburide 500/2.5 mg) as evidenced by the maintenance of the mean HbA$_{1c}$ levels from Week 20 (6.64%, 6.79%, 6.68%, 6.44%) to Week 32 (6.78%, 6.96%, 6.87%, 6.68%) of double-blind therapy below the therapeutic target of 7% (FIGS. 3 and 4).

Interim open-label first line therapy data demonstrate that for subjects directly enrolled, the mean HbA$_{1c}$ at baseline was 10.6%, and for the subset of subjects with available data, a mean decrease of 3.5% in HbA$_{1c}$ was achieved with a mean HbA$_{1c}$ of 7.1% through 26 weeks. Of the subjects directly enrolled into open-label therapy, 87% received the medium dose 500/2.5 mg fixed combination as initial therapy and at the time of the interim report, the mean dose of fixed combination therapy was metformin/glyburide 1569/7.85 mg. For subjects with available open-label data completing the double-blind treatment phase and continuing into the open-label treatment phase, the mean HbA$_{1c}$ at baseline was 8.32%. For all subjects reaching 13 weeks of therapy, a mean decrease of 1.76% in HbA$_{1c}$ was achieved with the mean HbA$_{1c}$ of 6.56%. Of the subjects completing the double-blind treatment phase and continuing into the open-label treatment phase, 78% received the low dose (250/1.25 mg) and 22% received the medium dose (500/2.5 mg) fixed combination as initial therapy. The mean dose of fixed combination therapy was metformin/glyburide 696/3.48 mg.

No clinically significant patterns of greater or reduced effect were apparent in any of the sub-populations (age, gender, race) with respect to response in HbA$_{1c}$ from baseline in either double-blind trial with fixed combination metformin/glyburide as first line therapy.

This clinical program also assessed fasting plasma glucose as a parameters of short term glycemic control. FPG results in double-blind studies were consistent with the HbA$_{1c}$ results. As first line therapy, statistically and clinically significant larger mean decreases in FPG for both fixed combination treatment groups compared to placebo and metformin were achieved (FIG. 6). An early response to fixed combination therapy was observed; differences among treatment groups were apparent by Week 2 of double-blind therapy as a time when subjects were still undergoing initial titration and were receiving only one-half potential maximum dosing. This early response at one-half maximum dosing in a monotherapy refractory patient population demonstrates the benefit of combination therapy for the patient and using combination therapy earlier in the disease process.

HemoglobinA$_{1c}$ is the prevailing standard measure of overall glycemic control and it is the glycemic marker found to be correlated with long term complications. Although, fasting plasma glucose, the current standard for the diagnosis of diabetes, is a faster, more convenient marker, it does not provide an optimal assessment of circadian glycemic control. It has been shown, and intuitively understood, that non-fasting plasma glucose is a better marker of diabetic control than FPG in type 2 diabetes; it also correlates better with HbA$_{1c}$. Postprandial hyperglycemia is an early marker of the metabolic defects found in type 2 diabetes and contributes to beta cell dysfunction. An important association between postprandial glucose levels and cardiovascular disease has been demonstrated. If normal glycemia is the goal in preventing long term complications of diabetes then monitoring and lowering postprandial glucose is a rational strategy in improving metabolic function and achieving overall glucose control.

As first line therapy, statistically significant larger mean decreases in absolute postprandial glucose (63–65 mg/dL) were observed for both fixed combination treatment groups than the placebo group. Larger mean decreases in absolute PPG were also achieved compared with gyburide (16–18 mg/dL) and metformin (18–20 mg/dL) monotherapy (FIGS. 8A and 8B). The 2-hour postprandial glucose excursion from a fasting baseline for both the low dose (22.5 mg/dL) and medium dose (23.9 mg/dL) fixed combination treatment groups was only 56%–59% of placebo (40.3 mg/dL), 59%–63% of glyburide (38.2 mg/dL) and 75%–81% of metformin (29.5 mg/dL), Evaluating the excursion rather than the absolute value demonstrates that glyburide is similar to placebo, metformin achieves better postprandial glucose lowering than glyburide and placebo, and that the low dose combination is the most powerful in lowering postprandial glucose excursion. As there is no published clinical data with combination therapy studied in a drug naive patient population, these results add new insight to understanding of the impact of treatment options at this stage of the disease. Indeed, the results could not have been predicted from the changes observed in the much studies second line therapy population.

Insulin levels were evaluated in the fasting and postprandial state in the first line therapy study (FIG. 7). There was a statistically significant increase in insulin response in the presence of a glucose load for both fixed combination treatment groups (24–28.8 µiu/mL) compared to placebo. A larger increase in insulin response in the presence of a glucose load for the low dose fixed combination (14.6 µiu/mL) treatment group was observed when compared to glyburide monotherapy and a larger increase in insulin response in the presence of a glucose load for both fixed combination (21–25.8 µiu/mL) treatment groups was observed when compared to metformin monotherapy. When considering the mean doses of active therapy per treatment group, the insulin response cannot be explained by the sulfonylurea component alone with fixed combination therapy. This clinical data supports preclinical work with isolated pancreatic islet cells where it has been suggested that metformin prevents the hyperglycemic desensitization of the islet cells. The combination of the physiologic and appropriate increased insulin response with a corresponding larger decrease in glucose excursion suggests that the combination is improving the efficiency of the pancreas in responding to a glucose load, preserving beta cell function and improving insulin sensitivity.

The essential goal in the management of patients with type 2 diabetes, in addition to aggressively treating elevated blood pressure and lipid levels, is achieving as near normal glycemic levels as possible or achieving glycemic therapeutic targets. There was a greater response to fixed combination therapy with respect to greater frequencies of subjects achieving therapeutic targets and greater decreases in absolute $HbA_{1c}$. As first line therapy, a higher frequency of subjects on fixed combination therapy (66%–71%) achieved a glycemic target of an $HbA_{1c}<7\%$ compared with 60% of sulfonylurea monotherapy, 50% of metformin monotherapy and 20% of placebo following 20 weeks of double-blind therapy. Approximately 28% of subjects in each fixed combination group had decreases in $HbA_{1c}$ from baseline greater than 2.0%, compared with 16%–17% of each monotherapy group and 3% of placebo. Of note, is that these targets were not achieved with simply higher total doses of medication, but with lower doses of the complementary components. Mean final doses achieved in each first line therapy treatment arm were approximately glyburide 5.3 mg, metformin 1307 mg, low dose fixed combination 557/2.78 mg and medium dose fixed combination 818/4.1 mg. For the change in $HbA_{1c}$ by number of tablets, the pattern observed with fixed combination therapy is not unexpected from a pathophysiologic viewpoint. It indicates that there is a clear response to target at all dose levels and that the need for higher doses correlates with a higher baseline $HbA_{1c}$. A similar pattern can be detected for glyburide up to a total dose 7.5 mg; no clear pattern was observed with metformin therapy.

The data presented supports low dose fixed combination metformin/glyburide as the first line agent most likely to bring a patient to therapeutic target, no matter how high their baseline $HbA_{1c}$. For both fixed combination therapies, the mean decrease from baseline $HbA_{1c}$ is larger for subjects with higher baseline levels. This phenomenon was not observed with glyburide, metformin or placebo and is not expected to be seen with other monotherapies. This demonstrates the contribution of components necessary for achieving therapeutic glycemic targets when baseline $HbA_{1c}$ level is greater than 9%. Monotherapy was shown to have a plateauing of glycemic response for baseline $HbA_{1c}$ levels <9% while fixed combination therapy had additional incremental decreases in $HbA_{1c}$ for baseline $HbA_{1c}$ levels <9%.

For all subjects enrolled into the open-label first line treatment phase with available data for at least two time points, the mean $HbA_{1c}$ at baseline was 9.45%. By Weeks 13, 26 and 39 approximately 50–55% of subjects had achieved an $HbA_{1c}$ of less than 7% and an additional 30% had achieved an $HbA_{1c}<8\%$. This response rate and magnitude of change in $HbA_{1c}$ lowering can be expected with combination therapy but is rarely seen with monotherapy antihyperglycemic agents. The fundamental issue is what initial antihyperglycemic treatment will achieve the glycemic target of an $HbA_{1c}<7\%$ in the greatest proportion of patients. This data strengthens the need for the reevaluation of current type 2 diabetes treatment paradigms and to shift to the use of combination therapy sooner in the disease process.

Weight gain is typically observed with all antihyperglycemic agents other than metformin monotherapy. With improved glycemic control, a weight gain is actually expected as calories are conserved rather than lost due to poor metabolic control. In this clinical program, as glycemic control improved, minimal early weight gain of approximately 1–2 kg was observed with fixed combination therapy; this was comparable to the 2 kg weight gain observed with first line glyburide monotherapy. In double-blind therapy, after the initial minimal gain, weight remained stable and did not continue to increase with time.

Overall there were no clinically or statistically significant differences between any of the treatment groups with respect to changes in the plasma lipid profile. As the most severe patients were excluded from the placebo controlled trial, smaller changes in response to therapy might be undetectable. The first line therapy patient population had inadequate glycemic control but diet and exercise has already succeeded in bringing the mean $HbA_{1c}$ to 8.2%. In subjects treated with fixed combination therapy, there was no adverse effect on the plasma lipid profile (total cholesterol, LDL, HDL, and triglycerides) or significant differences compared with placebo or either glyburide and metformin monotherapy.

With better understanding of the relationship between diabetes control and long-term complication rate the goal of diabetes management today is to achieve and maintain as near normal glycemia as possible. Targeting multiple defects using agents with synergistic or complementary mechanisms of action intuitively makes sense to achieve a therapeutic glycemic target. Improved understanding of the natural history of type 2 diabetes suggests that current treatment paradigms of allowing "failure" to occur prior to implementing a more aggressive treatment strategy should be reassessed. Earlier use of low dose combination therapy, particularly when the use of lower doses results in better tolerability, therefore appears to be an important therapeutic approach if targets are to be achieved and compliance maintained. The fixed combination evaluated in this study allows for lower dosing and the ease of use in a single entity.

Low dose fixed combination metformin/glyburide therapy is safe and effective in achieving and maintaining glycemic control in patients with type 2 diabetes who have inadequate glycemic control with diet and exercise. The use of combination therapy earlier in the diabetes disease progression appears to be a clinically sound alternative to the classic treatment paradigms of allowing failure of step wise therapy before instituting a more aggressive, but clinically sound, treatment strategy. Though not evaluated in this short-term study, the strategy to achieve as near normal glycemic targets as possible is likely to have an impact in slowing the progression of the diabetes disease process and delay the onset of long-term diabetes complications. Given a refractory monotherapy patient population the fixed combination of metformin and glyburide was associated with a clinically significant improvement in glycemic control without evidence of detrimental metabolic effects or safety concerns. There was no clinically significant hypoglycemia, no negative impact in plasma lipids and a limited early weight gain followed by stable weight with time. The synergism of the metformin and sulfonylurea combination is an established one; a fixed combination of metformin and glyburide is effective in improving glycemic control and is a rationale choice in the antihyperglycemic armamentarium. It is assumed that a fixed combination simplifies dosing, is more convenient and therefore may lead to better compliance with therapy.

The low dose (250/1.25 mg) fixed combination would be the initial starting dose as first line therapy in drug naive subjects. This should then be titrated as indicated to achieve a $HbA_{1c} < 7\%$.

Overall Conclusions

The safety and efficacy data presented from this clinical program assessing fixed combination metformin/glyburide as first line therapy in patients with type 2 diabetes confirm the following:

The percentages of subjects who discontinue from therapy because of hyperglycemia were lower for fixed combination metformin/glyburide compared with metformin, glyburide, and placebo.

Hypoglycemia and symptoms of hypoglycemia, as first line therapy (FIG. 9), occurred less often with metformin/glyburide 250/1.25 mg compared to metformin/glyburide 500/2.5 mg and glyburide.

As first line therapy, the incidence of gastrointestinal adverse events associated with fixed combination was lowest for metformin/glyburide 250/1.25 mg compared with metformin/glyburide 500/2.5 mg and metformin (FIG. 10).

No new or unexpected adverse events or laboratory abnormalities occurred in subjects who received long-term open-label fixed combination metformin/glyburide.

Significantly better efficacy of fixed combination metformin/glyburide at any dose strength as evidenced by greater reductions of all glycemic parameters ($HbA_{1c}$, postprandial glucose, fasting glucose and fructosamine) compared to placebo, glyburinde and metformin therapy.

A synergistic effect of the low dose combination in targeting multiple metabolic defects to improve beta cell function and insulin sensitivity, as evidenced by postprandial plasma glucose and insulin excursions, to achieve improved metabolic function and glycemic control.

A higher frequency of patients on fixed combination metformin/glyburide therapy achieved a glycemic therapeutic target of an $HbA_{1c} \leq 7\%$.

Efficient glycemic lowering to therapeutic targets for any baseline $HbA_{1c}$ compared with placebo, glyburide and metformin therapy. As initial therapy, glyburide and metformin were shown to have a plateauing of glycemic response for baseline $HbA_{1c}$ levels >9% while fixed combination metformin/glyburide therapy had additional incremental decreases in $HbA_{1c}$ for baseline $HbA_{1c}$ levels >9%.

Limited early weight gain paralleling improved glycemic control, comparable to glyburide monotherapy; however, weight remained stable with time.

No adverse effect of the fixed combination therapies on the lipid profile (total cholesterol, LDL, HDL, and triglycerides) or significant differences from placebo or either glyburide and metformin monotherapy.

The favorable efficacy and tolerability of fixed combination metformin/glyburide 250/1.25 mg supports its use as the initial starting dose in first line therapy.

The above results clearly show that treating diabetes with the low dose metformin/glyburide formulation of the invention (250 mg/1.25 mg) is at least equivalent in efficacy to the higher dosage form (500 mg/2.5 mg), while resulting in reduced side effects.

What is claimed is:

1. A method for first line treatment of type 2 diabetes in a drug naive human patient, which comprises administering a drug to a drug naive human patient in need of treatment, as first line therapy, a therapeutically effective low dose of a pharmaceutical formulation comprising a low dose combination of metformin and at least one or more other antidiabetic agent, which is one or more of a glucosidase inhibitor, a glucagon-like peptide-1 (GLP-1), insulin, a PPAR α/γ dual agonist other than a thiazolidinedione, a meglitimide and an aP2 inhibitor, which provides at least substantially equivalent efficacy in treating diabetes in drug naive patients, but with substantially reduced side effects, as compared to metformin and said other antidiabetic agent employed in substantially higher daily dosages, wherein the dose of metformin is in an amount to provide a daily dosage within the range from about 160 mg to about 750 mg.

2. The method as defined in claim 1 wherein the other antidiabetic agent in said low dose formulation is one or more of a glucosidase inhibitor, a glucagon-like peptide-1 (GLP-1), insulin, or a PPAR α/γ dual agonist other than a thiazolidinedione.

3. The method as defined in claim 1 wherein the other antidiabetic agent in said low dose formulation is one or more of acarbose or insulin.

4. A method for lowering blood glucose in a hyperglycemic human patient, which comprises administering to a human patient in need of treatment a therapeutically effective amount of a low dose pharmaceutical formulation comprising a low dose combination of metformin and at least one or more other antidiabetic agent, which is one or more of a glucosidase inhibitor, a glucagon-like peptide-1 (GLP-1), insulin, a PPAR α/γ dual agonist other than a thiazolidinedione, a meglitimide and an aP2 inhibitor, which provides at least substantially equivalent efficacy in treating diabetes in drug naive patients, but with substantially reduced side effects, as compared to combinations of metformin and the other antidiabetic agent, employed in substantially higher daily dosages, wherein the dose of metformin is in an amount to provide a daily dosage within the ran e from about 160 mg to about 750 mg.

5. A method for decreasing insulin resistance, decreasing hemoglobin$A_{1c}$, increasing post-prandial insulin levels or decreasing post-prandial glucose excursion, in a diabetic human patient, which comprises administering to a human patient in need of treatment a low dose pharmaceutical formulation comprising a low dose combination of metformin and at least one or more other antidiabetic agent, which is one or more of a glucosidase inhibitor, a glucagon-like peptide-1 (GLP-1), insulin, a PPAR α/γ dual agonist other than a thiazolidinedione, a meglitimide and an aP2 inhibitor, which provides at least substantially equivalent efficacy in treating diabetes in drug naive patients, but with substantially reduced side effects, as compared to combinations of metformin and the other antidiabetic agent, employed in substantially higher daily dosages, wherein the dose of metformin is in an amount to provide a daily dosage within the range from about 160 mg to about 750 mg.

6. The method as defined in claim 4 wherein the human patient is a drug naive patient and the low dose formulation is administered as first line therapy.

7. The method as defined in claim 4 wherein the metformin is said low dose formulation is administered in an amount within the range from about 160 to about 400 mg 1 to 4 times daily, with a maximum daily dosage of metformin of about 750 mg and a minimum daily dosage of metformin of about 225 mg.

* * * * *